(12) United States Patent
Fritig et al.

(10) Patent No.: US 6,770,303 B1
(45) Date of Patent: Aug. 3, 2004

(54) USE OF ANTIFUNGAL AND/OR ANTIBACTERIAL AND/OR ANTIVIRAL COMPOUNDS

(76) Inventors: Bernard Fritig, Sauffelwegersheim (FR); Marguerite Kopp, Wolxheim (FR); Patrick Saindrenan, Strasbourg (FR); Marie-Pascale Latorse, Sourcieux les Mines (FR); Gilbert Labourdette, Paray le Monial (FR)

( * ) Notice: Subject to any disclaimer, the term of this patent is extended or adjusted under 35 U.S.C. 154(b) by 0 days.

(21) Appl. No.: 09/673,311
(22) PCT Filed: Apr. 12, 1999
(86) PCT No.: PCT/FR99/00844
§ 371 (c)(1), (2), (4) Date: Dec. 6, 2000
(87) PCT Pub. No.: WO99/53761
PCT Pub. Date: Oct. 28, 1999

(30) Foreign Application Priority Data

Apr. 16, 1998 (FR) .............................. 98 05043
Feb. 11, 1999 (FR) .............................. 99 01811

(51) Int. Cl.$^7$ .............................................. A61K 33/42
(52) U.S. Cl. .......................................... 424/603; 514/1
(58) Field of Search .............................. 424/603; 514/1

(56) References Cited

U.S. PATENT DOCUMENTS

| | | | |
|---|---|---|---|
| 5,780,469 A | * | 7/1998 | Ruess |
| 5,906,986 A | * | 5/1999 | Latorse |
| 5,948,783 A | * | 9/1999 | Pees et al. |
| 6,031,153 A | * | 2/2000 | Ryals et al. |
| 6,117,876 A | * | 9/2000 | Pees et al. |

FOREIGN PATENT DOCUMENTS

| | | |
|---|---|---|
| DE | 231482 | 1/1986 |
| DE | 19633502 | 2/1998 |
| EP | 0156729 A2 * | 10/1985 |
| FR | 2576749 | 8/1986 |
| FR | 2748631 | 11/1997 |
| FR | 2751845 | 2/1998 |
| GB | 2279252 | 1/1995 |
| JP | 07048214 | 2/1995 |
| JP | 09143013 | 6/1997 |
| WO | 9106312 | 5/1991 |
| WO | 9701277 | 1/1997 |
| WO | 9714310 | 4/1997 |
| WO | 9829537 | 7/1998 |
| WO | 9846078 | 10/1998 |

OTHER PUBLICATIONS

Heaney et al., ICIA0001: a novel fungicide for use against diseases on vines (1988) Proc. Br. Crop Prot. Conf. Pest Dis., vol. 1, pp. 245–250.*

Soyez, A new concept in crop protection: an adjuvant for fungicides–the case for coper tallate (1992) Proc. Br. Crop Prot. Conf. Pest Dis., vol 1, pp. 451–456.*

Cohen et al., Joint action of fungicides in mixtures: theory and practice (1990) Phytoparasitica, vol. 18, No. 2, pp. 159–169.*

Nash, Weed Science 29(2): 147–155 (1981).*

Kaestner et al., "Chitinase in cucumber hypocotyls is induced by geminating fungal spores and by fungal elicitors in synergism with inducers of acquired resistance", Plant Journal, vol. 13, No. 4, Feb. 1998, pp. 447–454 Abstract only.

Katz, et al., "A benzothiazdiazole primes parsley cells for augmented elicitation of defense responses", Plant Physiol., vol. 117, No. 4, 1998, pp. 1333–1339 Abstract only.

Chemical Abstracts, vol. 124, No. 21, May 20 1996, abstract No. 284531, T.L. Graham et al., "Signaling in soybean phenylpropanoid responses. Dissection of primary, secondary, and conditioning effects of light, wounding, and elicitor treatments", Plant Physiol. vol. 110, No. 4, 1996, pp. 1123–1133 Abstract only.

Kauss et al., "Pretreatment of parsley suspension cultures with salicylic acid enhances spontaneous and elicited produciton of H2O2", Plant Physiology, vol. 108, No. 3, 1995, pp. 1171–1178 Abstract only.

Kauss et al., "Pretreatment of parsley (Petroselinum crispum L.) suspension cultures with methyl jasmonate enhances elicitation of activated oxygen species", Plant Physiology, vol. 105, No. 1, 1994, pp. 89–94 Abstract only.

Kauss et al., "Methyl jasmonate conditions parsley suspension cells for increased elicitation of phenylproopaniod defense responses", Biochemical and Biophysical Research Communications, vol. 189, No. 1, 1992, pp. 304–308 Abstract only.

Joubert et al., "A beta 1–3 glucan specific to a marine alga, stimulates plant defence reactions and induces a broad range resistance against pathogens", Proc. Br. Crop. Prot. Conf. Pests Dis., vol. 2, 1998, pp. 441–448 Abstract only.

Steveni et al., "Some Properties of a Seaweed Extract Based on Ascophyllum nodosum when Sprayed, In Conjunction with an Adjuvant or Fungicide, on to a Barley Crop Infected with Erysiphe graminis (Cereal Mildew)", & J. Sci. Food Agric., vol. 63, No. 1, 1993, p. 128 Abstract only.

* cited by examiner

*Primary Examiner*—Jean C. Witz

(57) ABSTRACT

Phosphorus acid derivatives and the like are used as an amplifier (potentiator) of plant defense responses induced by other materials (elicitors).

9 Claims, 11 Drawing Sheets

USE OF ANTIFUNGAL AND/OR ANTIBACTERIAL AND/OR ANTIVIRAL COMPOUNDS

This application is a 371 of PCT/FR99/00844, filed Apr. 12, 1999, which claims priority to French application Serial No. 98/05043, filed Apr. 16, 1998 and to French application Serial No. 99/01811, filed Feb. 11, 1999.

The present invention relates to the novel use of one or more derivatives B as amplifiers (potentiators) of the physiological responses of plants, for example the defense responses of plants to pathogens. The application of one or more "elicitors" A makes it possible to induce a certain level of defense in the plant. It has been found that the use of certain compounds B, for example antifungal and/or antibacterial and/or antiviral agents, makes it possible to amplify these responses obtained by the use of elicitors A alone.

The natural defense mechanisms induced in plants, the standard model of which is the hypersensitivity reaction (HR), consist of a complex cascade of events involving the perception of the microbe or of a microbial compound (elicitor) by the plant, the death of the cells attacked and the production of various chemical signals and messengers. These chemical signals and messengers induce metabolic changes associated with active defense: activation of phenylalanine ammonia lyase (PAL), which is a key enzyme in the phenylpropanoid pathway leading to the biosynthesis of aromatic compounds with antibiotic activity (phytoalexins), signal molecules such as salicylic acid (SA) or structural molecules (lignin); activation of the octadecanoic pathway and in particular of lipoxygenase (LOX) which is capable of generating hydroperoxide radicals and free radicals involved in cell death, or signal molecules such as jasmonic acid.

The term "potentiating effect" means a sensitization activity of the plant or of cells to respond in a greatly amplified manner to a subsequent stress factor, for example a treatment with an elicitor. A potentiator will thus be a compound (a molecule) and/or a mixture of compounds which sensitizes the plant to respond in an amplified manner when one or more) other elicitor molecule(s) is (are) applied. It has been found that this potentiator can itself possess elicitor properties.

The elicitor compound A is chosen from the list of compounds comprising proteins, oligosaccharides (for example such as trehalose), polysaccharides (for example such as the product Elexa™, a registered trade mark of Agricultural Glycosystems Inc. or Chitosan™), lipids, glycolipids, glycoproteins, peptides of diverse origin, algal extracts, extracts from the walls of plant material (for example algal extracts) and/or of fungal material, fungi, Bion™ (registered trade mark of Novartis for the compound BTH or CGA 245704) and/or one of its analogues (in particular those known from European patent EP 313,512 and European patent application EP 0,690,061), yeast extracts, salicylic acid and/or one or more of its esters.

The elicitor compound A is preferably one (or more) algal extracts (hydrolysates) such as, for example, the oligopectins described in document WO 98/47375, which is incorporated herein by reference.

Even more advantageously, the list, which is not exhaustive, of algae which can be used in the context of the present invention are algae which may be sold by the company Agrocean, such as, for example, Agrimer 540, CAL, Agrotonic, Laminaria sp. (*Laminaria digitalis, Laminaria saccharina, Laminaria hyperborea*), Ascophyllum sp. (*Ascophyllum nodosum*), Himanthalla sp. (*Himanthalla elongata*), Undaria sp. (*Undaria pinnatifida*), Fucus sp. (*Fucus vesiculum*), Ulva sp. and Chondrus sp. and Enteromorphe sp.

The potentiating compound B is chosen from the list of compounds comprising phosphorous acid derivatives, for instance metal phosphites such as fosetyl-Al, fosetyl-Na and phosphorous acid itself and its alkali metal or alkaline-earth metal salts, Bion™ (BTH or CGA 245704) and/or one of its analogues, the product Elexa™, INA (isonicotinic acid), ABA (aminobutyric acid) and methyl jasmonate (MeJa).

Fosetyl-Al and phosphorous acid have mainly been selected as potentiators in the biological experimentation, but, for reasons of toxicity of fosetyl-Al on tobacco cell cultures, we replaced it with fosetyl sodium in the cell tests.

The use of a simplified model system such as cell cultures treated with elicitors of varied nature makes it possible to mimic the HR completely, while at the same time being rid of the spatial component inherent in the whole plant, and allows access to early intracellular signalling events. This invention addresses the problem of potentiating the defense responses with chemical substances.

Elicitors belonging to different protein and saccharide categories were chosen, but are not the same for the cell tests and biological tests on plants.

Bion™ (BTH) is the reference elicitor product chosen, and the reason for which the powdery mildew/wheat pair was selected in the preliminary biological manipulations performed.

In order to dissect the phenomena induced by applying the potentiator, on the one hand, and the elicitor, on the other hand, all of the preliminary tests concern sequential treatments (separated over time) between potentiator and elicitors. This does not exclude the two types of products from being mixed together or from being used simultaneously (although not as mixtures).

The various elicitors (parietal fragments of *Phytophthora megasperma* H20, pectin oligomers, an elicitin produced by *P. megasperma*, β-megaspermine) are prepared in water. The pH of the solutions is adjusted to about 5.5, if necessary.

The phosphorous acid, the fosetyl-Na, the fosetyl-Al, the salicylic acid ester and the product Elexa™ (E) are prepared in water. The BTH is prepared in DMSO for the tests on tobacco cells and is used in the commercial form Bion™ (or Bendicar™) for the tests on plants.

Lastly, elicitors can also have a potentiating effect with respect to other elicitors, as is the case with BTH or Elexa™.

The present invention relates particularly to the novel use of phosphorous acid and/or one of its derivatives as an amplifier (potentiator) of the defense responses of plants.

The present invention relates in particular to the potentiating effect of phosphorous acid ($H_3PO_3$) and fosetyl-Na, as well as of Bion™, on the defense responses of tobacco (induction of PAL and LOX activities, production of SA) after applying elicitors of various natures such as i) oligosaccharides of β-glucan type isolated from the walls of *Phytophthora megasperma* (*Pmg*), ii) pectin oligomers, iii) β-megaspermine, a protein secreted by *P. megasperma* H2O.

The present invention relates in particular to the potentiating effect of phosphorous acid ($H_3PO_3$) and fosetyl-Al, as well as Elexa™, on the responses obtained, in the context of biological tests, by applying elicitors of diverse nature (algal extract, Elexa™, Bion™, salicylic acid and/or ester, yeast extract, trehalose or killed or live spores of a non-host fungus (barley powdery mildew spores)).

It is clearly understood, and also included in the context of the present invention, that the use described above can optionally be coupled with a conventional fungicidal treatment using a known fungicide, it being possible for this treatment to take place simultaneously with or separately from the applications of A and/or B.

A subject of the present invention is also a synergistic antifungal and/or antibacterial and/or antiviral composition comprising an elicitor and a phosphorous acid derivative, and a process using the said composition and intended to curatively or preventively protect crops against fungal attack.

It is always desirable to improve the spectrum of activity and the efficacy of such compounds of antifungal action, or to strengthen them by combining them with other molecules in order to obtain a product which gives better performance, or alternatively to prevent the appearance of fungal strains which are resistant to these novel antifungal agents.

It is also very desirable to have available antifungal products which benefit from an improved persistence of action so as to space out over time the number of plant-protection treatments required for the correct control of parasites.

It is particularly advantageous in all cases to be able to reduce the amount of chemical products distributed into the environment, while at the same time ensuring high-performance protection of crops against fungal attack.

It has now been found that one (or more) of the above objectives can be achieved by virtue of the present invention.

A subject of the present invention is also a synergistic antifungal and/or antibacterial and/or antiviral composition comprising, as compound A, one or more elicitors of diverse origin and nature, and at least one antifungal compound B chosen from the group comprising phosphorous acid derivatives, for instance metal phosphites such as fosetyl-Al, fosetyl-Na, phosphorous acid itself and/or its alkali metal or alkaline-earth metal salts, one or more elicitor compounds also possessing potentiating properties.

It is clearly understood that the said antifungal and/or antibacterial and/or antiviral composition can contain a single compound B or more than one such compound, for example 1, 2 or 3 compounds B depending on the use for which it is intended.

Among the meanings more especially preferred for compound B defined above, further preference is given to fosetyl-Al.

In an entirely unexpected manner, the composition according to the invention appreciably improves the action of active materials taken separately for a number of fungi which are particularly harmful to monocotyledon crops such as, in particular, wheat, rice and barley, and dicotyledon crops such as, in particular, grapevine and solanacea plants. This improvement is reflected in particular in a reduction of the doses of each of the constituents, which is particularly advantageous for the user and the environment.

The antifungal and/or antibacterial and/or antiviral mixture (applied simultaneously or separately) thus has synergistic properties, confirmed by applying the method defined by Limpel, L. E., P. H. Schuldt and D. Lammont, 1962, Proc. NEWCC 16:48–53, using the following formula, which is also referred to as the Colby formula:

$$E=X+Y-X \cdot Y/100$$

in which:
E is the expected percentage inhibition of growth of the fungus by the mixture of the two antifungal agents A and B at defined doses, equal to a and b respectively;
X is the percentage inhibition observed for the antifungal and/or antibacterial and/or antiviral compound A at the dose a,
Y is the percentage inhibition observed for the antifungal and/or antibacterial and/or antiviral compound B at the dose b.

When the percentage inhibition observed for the mixture is greater than E, there is synergism.

The structures corresponding to the common names of the active materials B are given in at least one of the following 2 books:
"The Pesticide Manual" edited by Clive Tomlin and published by the British Crop Protection Council, 11th edition (page 629);
the Index Phytosanitaire 1998, published by the Association de Coordination Technique Agricole, 34th edition.

The antifungal and/or antibacterial and/or antiviral composition according to the invention comprises, as active material, a compound A and at least one compound B mixed with agriculturally acceptable solid or liquid supports and/or surfactants which are also agriculturally acceptable. The usual inert supports and the usual surfactants can be used in particular. These compositions include not only compositions ready to be applied to the crop to be treated by means of a suitable device, such as a spraying device, but also commercial concentrated compositions which must be diluted before being applied to the crop. The term "active material" denotes the combination of at least one compound A with at least one compound B.

These compositions can also contain other ingredients of any kind such as, for example, other known fungicides, protective colloids, adhesives, thickeners, thixotropic agents, penetrating agents, stabilizers, sequestering agents, etc. More generally, the compounds A and B can be combined with any solid or liquid additive which complies with the usual formulation techniques.

In general, the compositions according to the invention usually contain from 0.05 to 95% (by weight) of active material, one or more solid or liquid supports and, optionally, one or more surfactants.

In the present specification, the term "support" denotes a natural or synthetic, organic or inorganic material with which the active material is combined to make it easier to apply to the aerial parts of the plant. This support is thus generally inert and should be agriculturally acceptable, especially on the treated plant. The support can be solid (clays, natural or synthetic silicates, silica, resins, waxes, solid fertilizers, etc.) or liquid (water, alcohols, in particular butanol, etc.).

The surfactant can be an emulsifier, a dispersing agent or a wetting agent of ionic or nonionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water.

Thus, the compositions for agricultural use according to the invention can contain the active material in a very wide range, from 0.05% to 95% (by weight). Their surfactant content is advantageously between 5% and 40% by weight. Except where otherwise indicated, the percentages given in this description, including the claims, are weight percentages.

These compositions according to the invention are themselves in quite diverse, solid or liquid forms.

As solid composition forms, mention may be made of powders for dusting (with an active material content which can be up to 100%) and granules, in particular those obtained by extrusion, by compacting, by impregnation of a granulated support or by granulation from a powder (the active material content in these granules being between 0.5 and 80% for the latter cases), tablets or effervescent lozenges.

The antifungal and/or antibacterial and/or antiviral composition according to the invention can also be used in the form of powders for dusting; a composition comprising 50 g of active material and 950 g of talc can also be used; a composition comprising 20 g of active material, 10 g of finely divided silica and 970 g of talc can also be used; these constituents are mixed together and ground and the mixture is applied by dusting.

As liquid composition forms or forms intended to constitute liquid compositions when applied, mention may be made of solutions, in particular water-soluble concentrates, emulsions, concentrated suspensions, aerosols and wettable powders (or powders for spraying), pastes and gels.

The concentrated suspensions, which can be applied by spraying, are prepared so as to obtain a stable fluid product which does not become deposited, and they usually contain from 10 to 75% of active material, from 0.5 to 15% of surfactants, from 0.1 to 10% of thixotropic agents, from 0 to 10% of suitable additives, such as antifoaming agents, corrosion inhibitors, stabilizers, penetrating agents and adhesives, and, as support, water or an organic liquid in which the active material is insoluble or only sparingly soluble: certain organic solid materials or inorganic salts can be dissolved in the support to help prevent sedimentation or as antifreezes for the water.

By way of example, a composition of a concentrated suspension is given below:

EXAMPLE CS1

| | |
|---|---|
| Active material | 500 g |
| Polyethoxylated tristyrylphenol phosphate | 50 g |
| Polyethoxylated alkylphenol | 50 g |
| Polysodium carboxylate | 20 g |
| Ethylene glycol | 50 g |
| Polyorganosiloxane oil (antifoaming agent) | 1 g |
| Polysaccharide | 1.5 g |
| Water | 316.5 g |

The wettable powders (or powders for spraying) are usually prepared such that they contain 20 to 95% of active material, and they usually contain, in addition to the solid support, from 0 to 30% of a wetting agent, from 3 to 20% of a dispersant and, when necessary, from 0.1 to 10% of one or more stabilizers and/or other additives, such as penetrating agents, adhesives, anticaking agents, dyes, etc.

In order to obtain the powders for spraying or wettable powders, the active materials are intimately mixed with the additional substances in suitable mixers and are ground with mills or other suitable blenders. Powders for spraying with advantageous wettability and suspension formation are thus obtained; they can be placed in suspension with water at any desired concentration and these suspensions can be used very advantageously, in particular for application to plant leaves.

Pastes can be prepared instead of wettable powders. The conditions and methods for preparing and using these pastes are similar to those for the wettable powders or powders for spraying.

By way of example, there follow various wettable powder compositions (or powders for spraying):

Example WP1

| | |
|---|---|
| Active material | 50% |
| Ethoxylated fatty alcohol (wetting agent) | 2.5% |
| Ethoxylated phenylethylphenol (dispersant) | 5% |
| Chalk (inert support) | 42.5% |

Example WP2

| | |
|---|---|
| Active material | 10% |
| Synthetic C13 oxo alcohol of branched type, ethoxylated with 8 to 10 ethylene oxide (wetting agent) | 0.75% |
| Neutral calcium lignosulphonate (dispersant) | 12% |
| Calcium carbonate (inert filler) | qs 100% |

Example WP3

This wettable powder contains the same ingredients as in the above example, in the following proportions:

| | |
|---|---|
| Active material | 75% |
| Wetting agent | 1.50% |
| Dispersant | 8% |
| Calcium carbonate (inert filler) | qs 100% |

Example WP4

| | |
|---|---|
| Active material | 90% |
| Ethoxylated fatty alcohol (wetting agent) | 4% |
| Ethoxylated phenylethylphenol (dispersant) | 6% |

Example WP5

| | |
|---|---|
| Active material | 50% |
| Mixture of anionic and nonionic surfactants (wetting agent) | 2.5% |
| Sodium lignosulphonate (dispersant) | 5% |
| Kaolinic clay (inert support) | 42.5% |

The aqueous dispersions and emulsions, for example the compositions obtained by diluting a wettable powder or an emulsifiable concentrate according to the invention with water, are included within the general scope of the present invention. The emulsions can be of the water-in-oil or oil-in-water type and they can have a thick consistency, such as that of a "mayonnaise".

The antifungal compositions according to the invention can be formulated in the form of water-dispersible granules, which are also included within the scope of the invention.

These dispersible granules, with an apparent density generally of between about 0.3 and 0.6, have a particle size generally of between about 150 and 2000 and preferably between 300 and 1500 microns.

The active material content of these granules is generally between about 1% and 90% and preferably between 25% and 90%.

The rest of the granulate is essentially composed of a solid support and optionally of surfactant adjuvants which give the granulate water-dispersibility properties. These granules can be essentially of two different types depending on whether the support selected is soluble or insoluble in water. When the support is water-soluble, it can be inorganic or, preferably, organic. Excellent results have been obtained with urea. In the case of an insoluble support, it is preferably inorganic, for example such as kaolin or bentonite. It is then advantageously accompanied by surfactants (in a proportion of from 2 to 20% by weight of the granule) more than half of which consists, for example, of at least one dispersant, which is essentially anionic, such as an alkali metal or alkaline-earth metal polynaphthalene sulphonate or an alkali metal or alkaline-earth metal lignosulphonate, the remainder consisting of nonionic or anionic wetting agents such as an alkali metal or alkaline-earth metal alkylnaphthalene sulphonate.

Moreover, although this is not essential, other adjuvants can be added, such as antifoaming agents.

The granulate according to the invention can be prepared by mixing together the required ingredients, followed by granulation according to several techniques which are known per se (granulator, fluid bed, sprayer, extrusion, etc.). The process generally ends by a crushing operation, followed by an operation of screening to the particle size chosen within the limits mentioned above. Granules obtained as above and then impregnated with a composition containing the active material can also be used.

Preferably, it is obtained by extrusion, by performing the process as indicated in the examples below.

Example DG1

Dispersible Granules

90% by weight of active material and 10% of urea pellets are mixed together in a mixer. The mixture is then ground in a toothed roll crusher. A powder is obtained, which is moistened with about 8% by weight of water. The wet powder is extruded in a perforated-roller extruder. A granulate is obtained, which is dried and then crushed and screened, so as to retain, respectively, only the granules between 150 and 2000 microns in size.

Example DG2

Dispersible Granules

The constituents below are mixed together in a mixer:

| | |
|---|---|
| Active material | 75% |
| Wetting agent (sodium alkylnaphthalene sulphonate) | 2% |
| Dispersant (polysodium naphthalene sulphonate) | 8% |
| Water-insoluble inert filler (kaolin) | 15% |

This mixture is granulated in a fluid bed, in the presence of water, and then dried, crushed and screened so as to obtain granules between 0.15 and 0.80 mm in size.

These granules can be used alone, or as a solution or dispersion in water so as to obtain the desired dose. They can also be used to prepare combinations with other active materials, in particular fungicides, these being in the form of wettable powders, granules or aqueous suspensions.

As regards the compositions adapted for storage and transportation, they more advantageously contain from 0.5 to 95% (by weight) of active material.

Another subject of the invention is a process for curatively or preventively, preferably preventively, controlling phytopathogenic fungi of crops and/or bacteria and/or viruses, characterized in that an effective and non-phytotoxic amount of a combination of one or more compounds A and at least one compound B, for example in an antifungal and/or antibacterial and/or antiviral composition according to the invention, is applied to the aerial parts of the plants. The overall process can also optionally involve an additional treatment using a known fungicide, this fungicide being applied simultaneously with or separately from the compounds A and/or B.

The phytopathogenic fungi of crops which can be controlled by this process are, in particular, those:

of the oomycetes group:
of the genus Phytophthora, such as *Phytophthora phaseoli*, *Phytophthora citrophthora*, *Phytophthora capsici*, *Phytophthora cactorum*, *Phytophthora palmivora*, *Phytophthora cinnamoni*, *Phytophthora megasperma*, *Phytophthora parasitica*, *Phytophthora fragariae*, *Phytophthora cryptogea*, *Phytophthora porri*, *Phytophthora nicotianae*, *Phytophthora infestans* (mildew in solanacea plants, in particular potato or tomato);
of the Peronosporacea family, in particular *Plasmopara viticola* (downy mildew of grapevine), *Plasmopara halstedei* (sunflower mildew), Pseudoperonospora sp. (in particular cucumber mildew (*Pseudoperonospora cubensis*) and downy mildew of hop (*Pseudoperonospora humuli*)), *Bremia lactucae* (mildew of lettuce), *Peronospora tabacinae* (downy mildew of tobacco), *Peronospora destructor* (mildew of onion), *Peronospora parasitica* (downy mildew of cabbage), *Peronospora farinosa* (downy mildew of endives and of beetroot).

of the adelomycetes (ascomycetes) group:
of the genus Alternaria, for example *Alternaria solani* (early blight of solanacea plants, and in particular of tomato and potato),
of the genus Guignardia, in particular *Guignardia bidwellii* (black rot of grapevine),
of the genus Venturia, for example *Venturia inaequalis* and *Venturia pirina* (apple scab and pear scab),
of the genus Oïdium, for example powdery mildew of grapevine (*Uncinula necator*); powdery mildew of legumes, for example *Erysiphe polygoni* (downy mildew of crucifers); *Leveillula taurica*, *Erysiphe cichoracearum* and *Sphaerotheca fuligena* (powdery mildew of cucumber, of compositae and of tomato);

*Erysiphe communis* (powdery mildew of beetroot and cabbage); *Erysiphe pisi* (powdery mildew of pea and of alfalfa); *Erysiphe polyphaga* (bean mildew and cucumber mildew); *Erysiphe umbelliferarum* (powdery mildew of umbelliferae, in particular of carrot); *Sphaerotheca humuli* (hop mildew); powdery mildew of wheat and barley (*Erysiphe graminis* forma specie *tritici* and *Erysiphe graminis* forma specie *hordei*), of the genus Taphrina, for example *Taphrina deformans* (peach leaf curl), of the genus Septoria, for example *Septoria nodorum* or *Septoria tritici* (septoria leaf blotch), of the genus Sclerotinia, for example *Sclerotinia sclerotirium,* of the genus Pseudocercosporella, for example *P. herpotrichoides* (cereal eyespot), of the genus *Botrytis cinerea* (grapevine, legumes and market garden crops, pea, etc.), of the genus *Phomopsis viticola* (necrosis of grapevine), of the Basidiomycetes group:

of the genus Puccinia, for example *Puccinia recondita* or *striiformis* (stripe rust of wheat), *Puccinia triticina* and *Puccinia hordei,* of the Rhizoctonia spp. family, for example *Rhizoctonia solani.*

The diseases of bacterial and viral origin which can be controlled by this process are, in particular:

fire blight, *Erwinia amylovora;* bacterial blight of stone fruit trees, *Xanthomonas campestris;* bacterial canker of pear, *Pseudomonas syringae;* bacterial blight of rice and cereals;

the viruses present on rice, legumes and cereals.

The crops envisaged in the context of the present invention are preferably cereals (wheat, barley, corn and rice) and legumes (bean, onion, cucurbits, cabbage, potato, tomato, capsicum, spinach, pea, lettuce, celery and endive), fruiting crops (strawberry and raspberry plants), arboriculture crops (apple, pear, cherry, ginseng and lemon trees, coconut palms and pecan, cacao, walnut, hevea, olive, poplar and banana trees), grapevine, sunflower, beetroot, tobacco and ornamental crops.

A classification made not in terms of fungi or bacteria targeted but rather target crops can be illustrated as below:

grapevine: powdery mildew (*Uncinula necator*), mildew (*Plasmopara viticola*), rot (*Botrytis cinerea*), necrosis (*Phomopsis viticola*) and black rot (*Guignardia bidwellii*), solanacea plants: mildew (*Phytophthora infestans*), early blight (*Alternaria solani*) and rot (*Botrytis cinerea*), legumes: mildews (Peronospora sp., *Bremia lactucae* and Pseudoperonospora sp.), early blight (Alternaria sp.), sclerotinia rot (Sclerotinia sp.), rot (*Botrytis cinerea*), foot rot or root rot (Rhizoctonia spp.), powdery mildew (Erysiphe sp., *Sphaerotheca fuliginea*), arboriculture crops: scab (*Venturia inaequalis* and *V. pirina*), bacterial diseases (*erwinia amylovora, xanthomonas campestris, pseudomonas syringae*), powdery mildew (*Podosphaera leucotricha*) and brown rot (*Monilia fructigena*), citrus fruit: scab (*Elsinoe fawcetti*), melanose (*Phomopsis citri*) and Phytophthora sp. diseases, wheat, as regards controlling the following seed diseases: fusaria (*Microdochium nivale* and *Fusarium roseum*), stinking smut (*Tilletia caries, Tilletia controversa* or *Tilletia indica*) and septoria disease (*Septoria nodorum*);

wheat, as regards controlling the following diseases of the aerial parts of the plant: cereal eyespot (*Pseudocercosporella herpotrichoides*), take-all (*Gaeumannomyces graminis*), foot blight (*F. culmorum, F. graminearum*), black speck (*Rhizoctonia cerealis*), powdery mildew (*Erysiphe graminis* forma specie *tritici*), rusts (*Puccinia striiformis* and *Puccinia recondita*) and septoria diseases (*Septoria tritici* and *Septoria nodorum*);

wheat and barley, as regards controlling bacterial and viral diseases, for example barley yellow mosaic;

barley, as regards controlling the following seed diseases: net blotch (*Pyrenophora graminea*, Bipolaris, *Pyrenophora teres* and *Cochliobolus sativus*), loose smut (*Ustilago nuda*) and fusaria (*Microdochium nivale* and *Fusarium roseum*);

barley, as regards controlling the following diseases of the aerial parts of the plant: cereal eyespot (*Pseudocercosporella herpotrichoides*), net blotch (*Pyrenophora teres* and *Cochliobolus sativus*), powdery mildew (*Erysiphe graminis* forma specie *hordei*), dwarf leaf rust (*Puccinia hordei*) and leaf blotch (*Rhynchosporium secalis*);

potato, as regards controlling tuber diseases (in particular *Helminthosporium solani, Phoma tuberosa, Rhizoctonia solani, Fusarium solani*) and certain viruses (virus Y);

cotton, as regards controlling the following diseases of young plants grown from seeds: damping-off and collar rot (*Rhizoctonia solani, Fusarium oxysporum*) and black root rot (*Thielaviopsis basicola*);

pea, as regards controlling the following seed diseases: anthracnose (*Ascochyta pisi, Mycosphaerella pinodes*), fusaria (*Fusarium oxysporum*), grey mould (*Botrytis cinerea*) and rust (*Uromyces pisi*);

rapeseed, as regards controlling the following seed diseases: *Phoma lingam* and *Alternaria brassicae*, rot (*Botrytis cinerea*) and sclerotinia (*Sclerotinia sclerotirium*);

corn, as regards controlling seed diseases: (Rhizopus sp., Penicillium sp., Trichoderma sp., Aspergillus sp., and *Gibberella fujikuroi*), leaf blights (Bipolaris) and fusaria (*Fusarium oxysporum*);

rice: foot rot or root rot (Rhizoctonia spp.), flax, as regards controlling the seed disease (*Alternaria linicola*);

banana: black sigatoka (*Mycosphaerella figiensis*), sward: rust, powdery mildew, leaf spot, telluric diseases (*Microdochium nivale*, Pythium sp., *Rhizoctonia solani, Sclerotinia homeocarpa*, etc.), forest trees, as regards controlling damping-off (*Fusarium oxysporum, Rhizoctonia solani*).

The antifungal and/or antibacterial and/or antiviral composition of the invention is applied by means of various treatment processes such as:

spraying a liquid comprising the said composition onto the aerial parts of the crops to be treated, dusting, incorporation of granules or powders into the soil, watering, injection into trees and/or dabbing (paints) and/or application in the form of patches (dressings), and incorporation into composts and/or nutrient solutions for soil.

The spraying of a liquid onto the aerial parts of the crops to be treated is the preferred treatment process.

The expression "effective and non-phytotoxic amount" means an amount of composition according to the invention which is sufficient to allow the control or destruction of the fungi or bacteria present or liable to appear on the crops, and which does not entail any appreciable phytotoxicity symptoms for the said crops. Such an amount can vary within a wide range depending on the fungus or bacterium to be controlled, the type of crop, the climatic conditions and the compounds included in the antifungal and/or antibacterial and/or antiviral composition according to the invention. This amount can be determined by systematic field trials, which are within the capabilities of those skilled in the art.

Lastly, the invention relates to a product comprising at least one compound A and at least one compound B for controlling phytopathogenic fungi and/or bacteria and/or viruses in an environment by simultaneous, sequential or separate application.

The examples which follow are given purely for the purposes of illustrating the invention, which they do not limit in any way.

Experiments were carried out as regards the physiological effects induced in the defense responses in tobacco cell crops by measuring the production of enzymes such as PAL and LOX and of salicylic acid, and regarding the antifungal protective effects in the case of powdery mildew of wheat+ downy mildew of grapevine pairs.

EXAMPLE 1

Physiological Effects

1) The Choice of Biochemical Markers on Tobacco Cells.

- Measurement of the activity of PAL (phenylalanine ammonia lyase): key enzyme in the phenylpropanoid pathway and more particularly in the lignification involved in defense reactions in plants (most particularly in monocotyledon plants).
- Measurement of the salicylic acid: signal molecule.
- Measurement of the activity of LOX (lipoxygenase) which is a key enzyme in the synthesis of jasmonic acid, another signal molecule.

2) Plant Material.

The cell suspensions used are suspensions of *Nicotiana tabacum* BY (bright yellow) obtained from Washington State University (Pullman, USA). They are cultured in the dark, at 24° C. with agitation (120 rpm) and subcultured every 7 days by transferring 10 ml of culture into 70 ml of fresh medium.

The composition of the culture medium is given per 1 liter:

Murashige et Skoog salts (Duchefa) 4.3 g
sucrose 30 g
B1 (thiamine) 1 mg
inositol 100 mg
$KH_2PO_4$ 1.47 mM The pH is adjusted to 5.8.

The cells are pretreated 5 days after subculturing (end of the exponential growth phase) and elicited on the 6th day. Two hours before pretreatment, 10 ml of cells are transferred into 25 ml conical flasks. For the phenylalanine ammonia lyase (PAL) and lipoxygenase (LOX) activity analyses and the determination of the salicylic acid (SA), the cells are harvested at the desired time by filtration on Whatman 3 M paper, frozen in liquid nitrogen and stored at −80° C. until the analysis.

3) Phenylalanine Ammonia Lyase (PAL) Activity.

The cells (0.5 g) are ground in 0.1 M pH 8.8 borate buffer in the presence of active charcoal and quartz. The grinding ratio is 1/5 (w/v). After centrifugation, 100 μl of cell extract are incubated for 1 h at 37° C. in the presence of 200 μl of 0.1 M pH 8.8 borate buffer and 100 μl of a mixture of 0.1 M pH 8.8 borate buffer and 300 μM L-phenylalanine (labelled and cold mixture); the final solution has a specific activity of 810,000 cpm/ml.

The reaction is quenched by adding a few drops of 9 N $H_2SO_4$. 2 ml of $H_2O$ are added. The reaction products are extracted by adding 2 ml of an ether/cyclohexane mixture (1/1, v/v). Since the phenylalanine is insoluble in this mixture, the reaction is counted on 1 ml in the presence of "multi-purpose" scintillation liquid.

4) Lipoxygenase (LOX) Activity.

The cells (250 mg) are ground in 0.5 ml of extraction buffer in the presence of quartz.

Extraction buffer:

0.1 M pH 6.8 Tris buffer
1% w/v PVP
0.04% $Na_2S_2O_5$
0.5 mM PMSF
3 mM EDTA
0.1% v/v Triton The ground mixture is centrifuged for 15 min at 4° C. and 13,000 rpm. 2.87 ml of 0.1 M pH 6.8 Tris buffer are added to the cell extract, followed by 30 μl of 10 mM linolenic acid. After stirring, the change in the OD is monitored at 234 nm.

5) Extraction and Assay of the Salicylic Acid (SA).

The samples (0.5 g) of tobacco cells or leaves are ground in liquid nitrogen and grinding is then continued in the presence of 0.8 ml of 90% methanol. A known amount of $^{14}$C-labelled SA (1 nCi, 54 mCi/mol, Sigma) is then added in order to estimate the yield for the recovery of the endogenous SA. The amount of labelled SA added is less than the detection threshold for the analysis. The methanolic extracts are stirred vigorously and centrifuged for 20 min at 13,000 rpm. The supernatant is recovered and the pellet is subjected to a second extraction with 100% methanol. After centrifugation, the two supernatants are pooled. The samples are then evaporated to dryness on a concentrator under vacuum. The dry extracts are taken up in 0.5 ml of water at 80° C.

The samples are brought to pH 2 by addition of 2 M HCl and are then heated at 80° C. for one hour. Next, the samples are subjected to two successive extractions with 2 volumes of ether. After extraction, the ether phases are pooled and the ether is evaporated off under a flow of nitrogen. The dry residues are dissolved in about 150 μl of loading buffer (20 mM pH 5 sodium acetate: acetonitrile, in proportions of 9:1 (v/v)). 20 ml of this mixture, to which are added 3 ml of scintillation liquid (Ready Gel, Beckmann), are taken for counting of the residual radioactivity, which allows calculation of the SA recovery yield. The contents of total SA determined correspond to the sum of the SA contents in free form and of the SA contents in conjugated form, the SA being released during the hydrolysis.

Quantitative Analysis by HPLC

50 μl of the samples taken up in the loading buffer are injected onto a C18 reverse phase column (Nova Pak Waters, 3.9×150 mm) equilibrated in the 97% sodium acetate (20 mM, pH 5)/3% acetonitrile mixture at a flow rate of 1 ml/min. The elution is programmed on a Waters HPLC system in an isocratic system for 10 min. The proportion of acetonitrile then increases up to 80% over 2 min, this proportion is maintained for 10 min, which allows washing of the column, which is then re-equilibrated in the starting mixture for 5 min, before a new injection. The SA is quantified by fluorometry (λ excitation=315 nm, λ emission=405 nm). The peak corresponding to this molecule is identified by comparison of the retention time with that of the reference SA (50 ng). The amounts of SA injected are calculated by means of comparing the area of the peaks corresponding to SA with that of the standard molecule injected. The SA contents in the samples are then calculated, taking the recovery yield into account.

Treatment Kinetics

In all cases, the pretreatment with the potentiator is carried out 18 hours before the elicitor treatment.

The samples for analysing the physiological effects are taken 4 hours, 12 hours or 24 hours after elicitation. The controls corresponding to a potentiation alone or an elicitation alone are systematically present for each sample taken.

Figure 1:
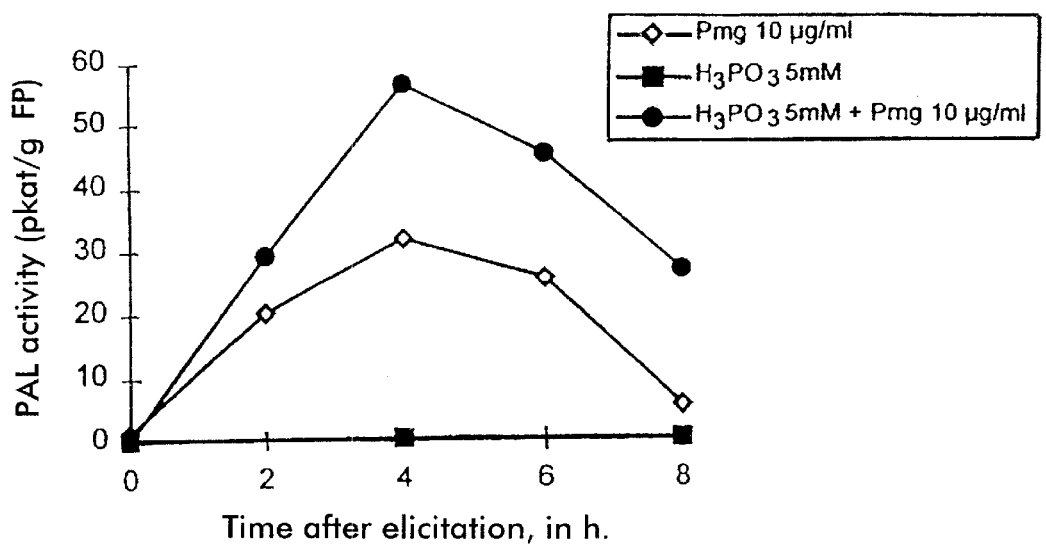
FIG. 1 shows the effect of conditioning with $H_3PO_4$ on induction with a first elicitor.

Results: Reference will be made at the end of the description to FIGS. 1 to 9, for which the following comments are given:

FIG. 1. Effect of conditioning the tobacco cell cultures with $H_3PO_3$ on the induction of the PAL activity after elicitation with an isolated Pmg oligosaccharide elicitor.

The cell cultures were conditioned (pretreatment) with 5 mM of $H_3PO_3$ for 18 h and induced with 10 µg/ml of oligosaccharide elicitor of β-glucan type. The elicitation per se entails a transient increase in the PAL activity, which returns to its initial level 8 h after applying the elicitor. A pretreatment of the cells with $H_3PO_3$ (5 mM) markedly amplifies the response to the elicitor (elicitability) and increases the durability of the phenomenon.

Figure 2:
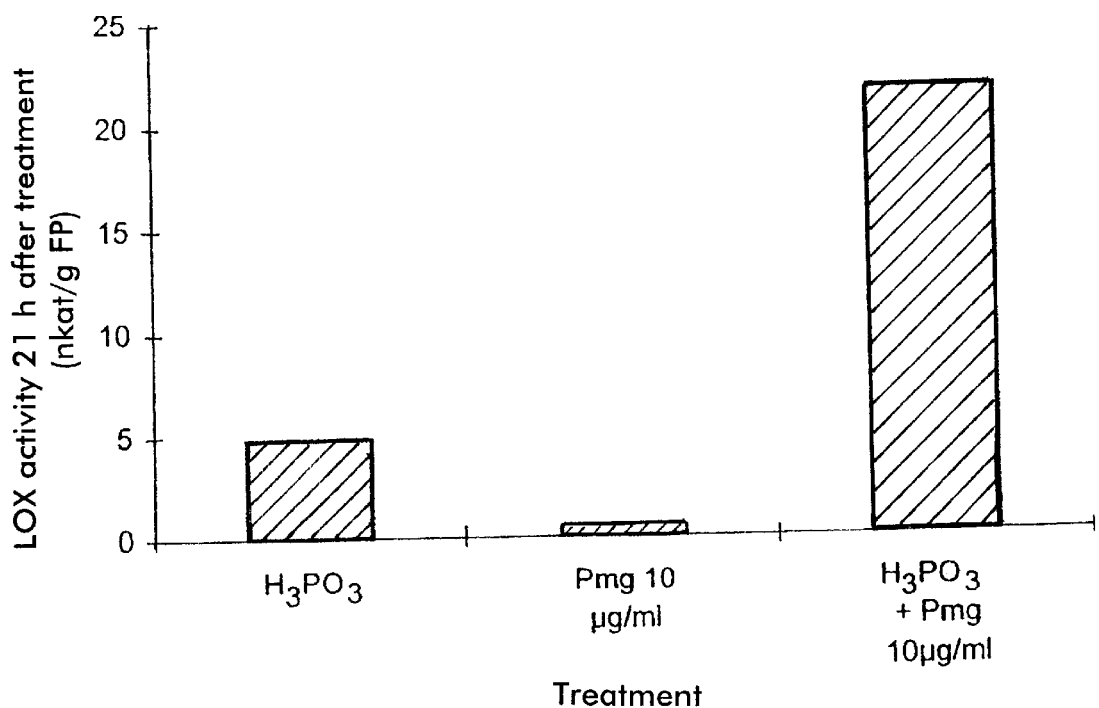
FIG. 2 shows the effect of $H_3PO_4$ on LOX.

FIG. 2. Effect of $H_3PO_3$ on the lipoxygenase (LOX) activity of tobacco cell cultures after induction with an isolated Pmg oligosaccharide elicitor.

The LOX activity was measured 21 h after elicitation with 10 µg/ml of oligosaccharide elicitor of β-glucan type. The effect of pretreating the cells with $H_3PO_3$ on the cell elicitability is large, since it makes it possible to induce an LOX activity which is about 4 times greater than that of the corresponding control. A mild inductive effect of the LOX activity can be observed 39 h (18 h of pretreatment+21 h) after applying the $H_3PO_3$ alone.

Figure 3:
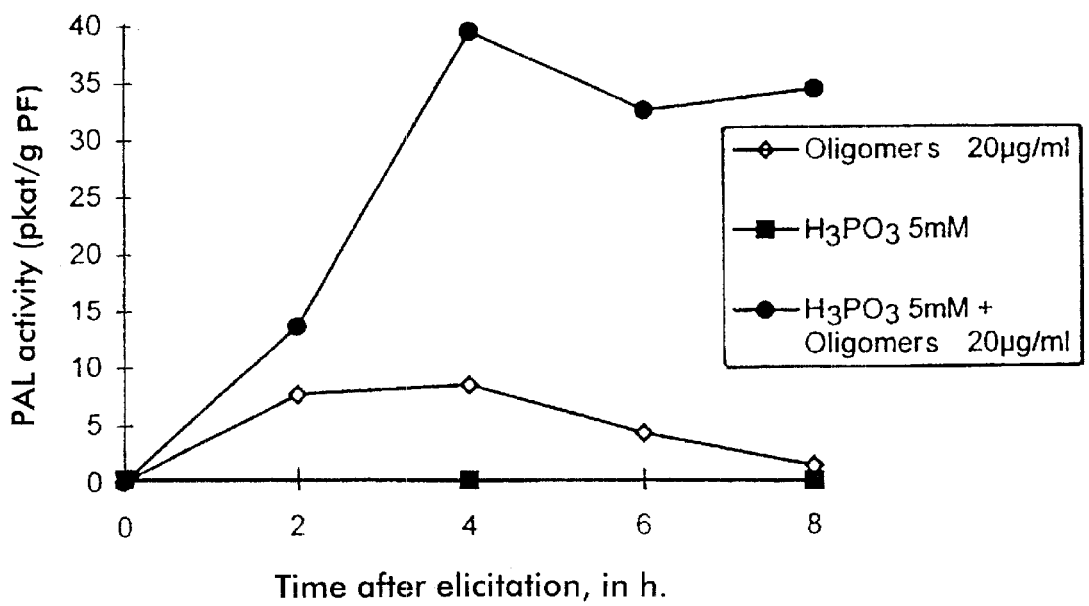
FIG. 3 shows the effect of conditioning with $H_3PO_4$ on induction with a second elicitor.

FIG. 3. Effect of conditioning the tobacco cell cultures with $H_3PO_3$ on the induction of the PAL activity after elicitation with pectin oligomers.

The cell cultures were conditioned with 5 mM of $H_3PO_3$ for 18 h and elicited with 20 µg/ml of pectin oligomers. Treatment of the cells with the elicitor entails a transient increase in the PAL activity, which returns to its initial level 8 h after elicitation. Conditioning of the cells with $H_3PO_3$ induces, after elicitation, a strong stimulation of the PAL activity, which remains at a high level throughout the experiment. No significant inductive effect as regards inducing the PAL activity can be detected after applying $H_3PO_3$ alone.

Figure 4:
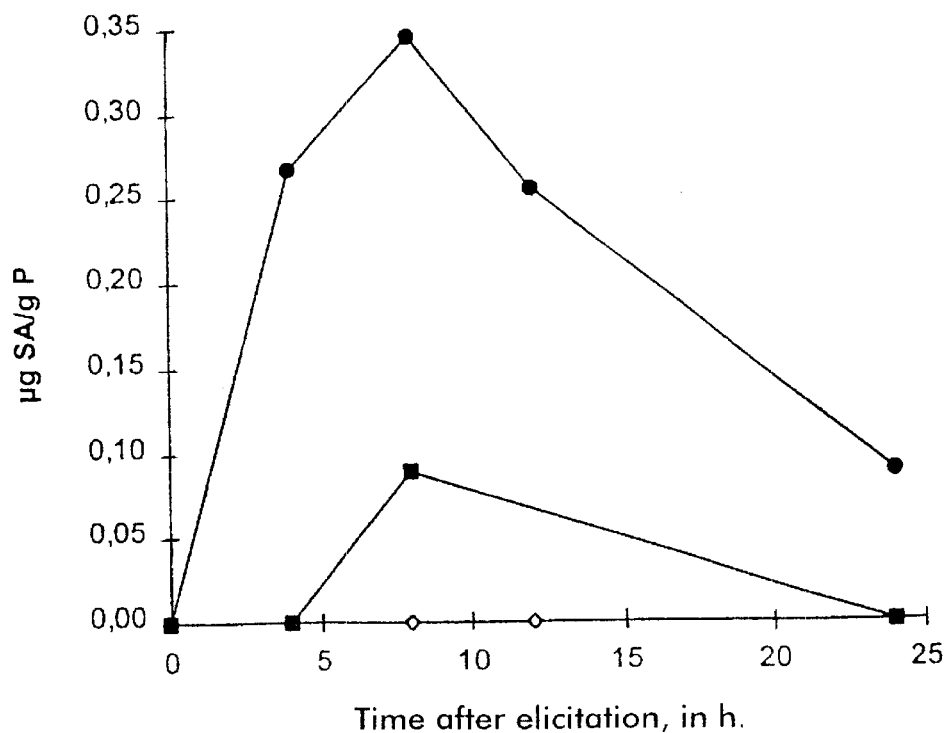
FIG. 4 shows the accumulation of SA.

FIG. 4. Accumulation of SA in tobacco cell cultures preconditioned with $H_3PO_3$ or otherwise and elicited with pectin oligomers.

SA is very transiently and weakly accumulated in response to elicitation with 20 µg/ml of pectin oligomers. Conditioning the cells with $H_3PO_3$, 18 h before the elicitation, entails a large increase in the rate of synthesis of SA relative to the unconditioned cells.

Figure 5:
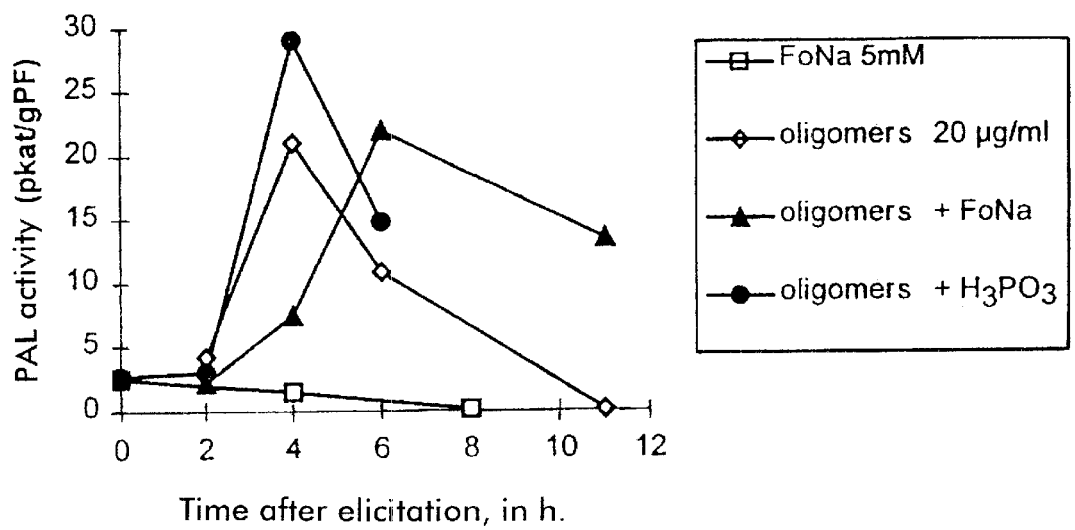
FIG. 5 shows the effect of conditioning with $H_3PO_4$ and fosetyl-Na on induction with a second elicitor.

FIG. 5. Effect of conditioning tobacco cell cultures with $H_3PO_3$ and fosetyl-Na on induction of the PAL activity after elicitation with pectin oligomers.

The cell cultures were conditioned with 5 mM of $H_3PO_3$ or fosetyl-Na for 18 h and elicited with 20 µg/ml of pectin oligomers. Treatment of the cells with the elicitor entails a transient increase in the PAL activity, which returns to its initial level 11 h after elicitation. Conditioning of the cells with $H_3PO_3$ induces, after elicitation, a stimulation of the PAL activity which is greater than that observed in the unconditioned cells. The fosetyl-Na maintains the PAL activity at a high level 11 h after the elicitation (durability effect). No significant effect of inducing the PAL activity can be detected after the application of fosetyl-Na alone.

Figure 6:
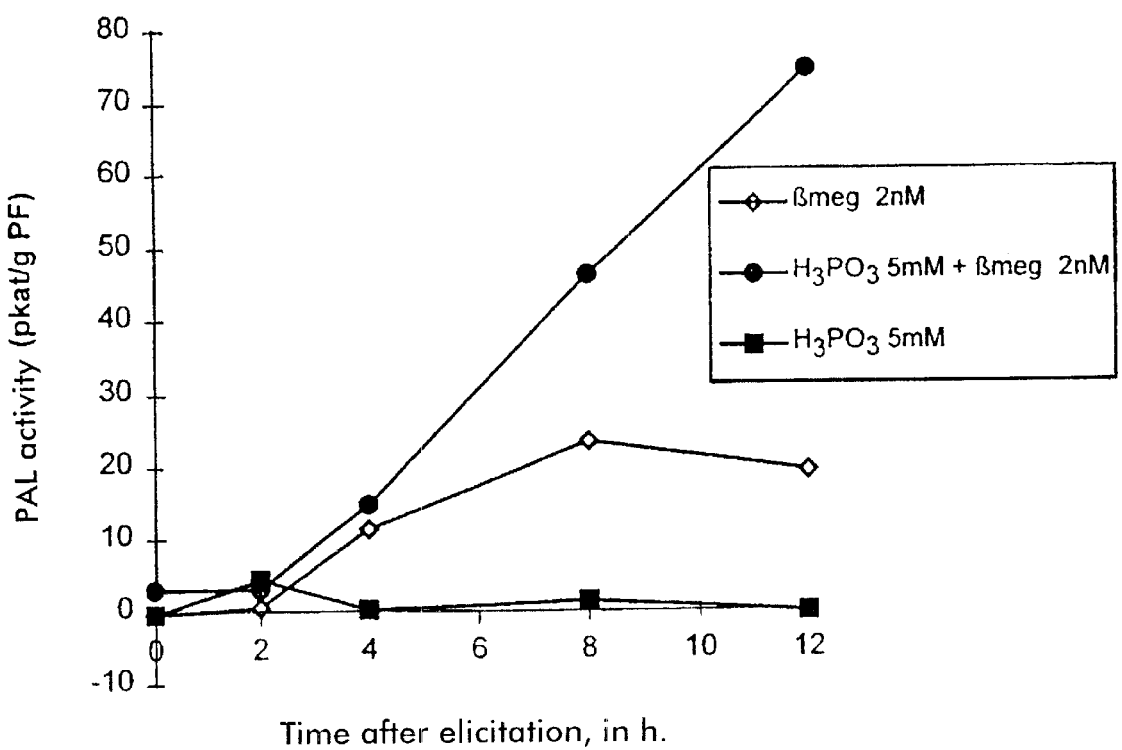
FIG. 6 shows the effect of conditioning with $H_3PO_4$ on induction with a third elicitor.

FIG. 6. Effect of conditioning tobacco cell cultures with $H_3PO_3$ on induction of the PAL activity after elicitation with 2 nM β-megaspermine.

The cell cultures were conditioned with 5 mM $H_3PO_3$ for 18 h and elicited with 2 nM β-megaspermine.

Application of the elicitor alone results in an increase in the PAL activity, which stabilizes 8 h after the elicitation. The PAL activity of the cells pretreated with $H_3PO_3$ increases linearly after elicitation, to reach 4 times the level of the unconditioned cells.

Figure 7:
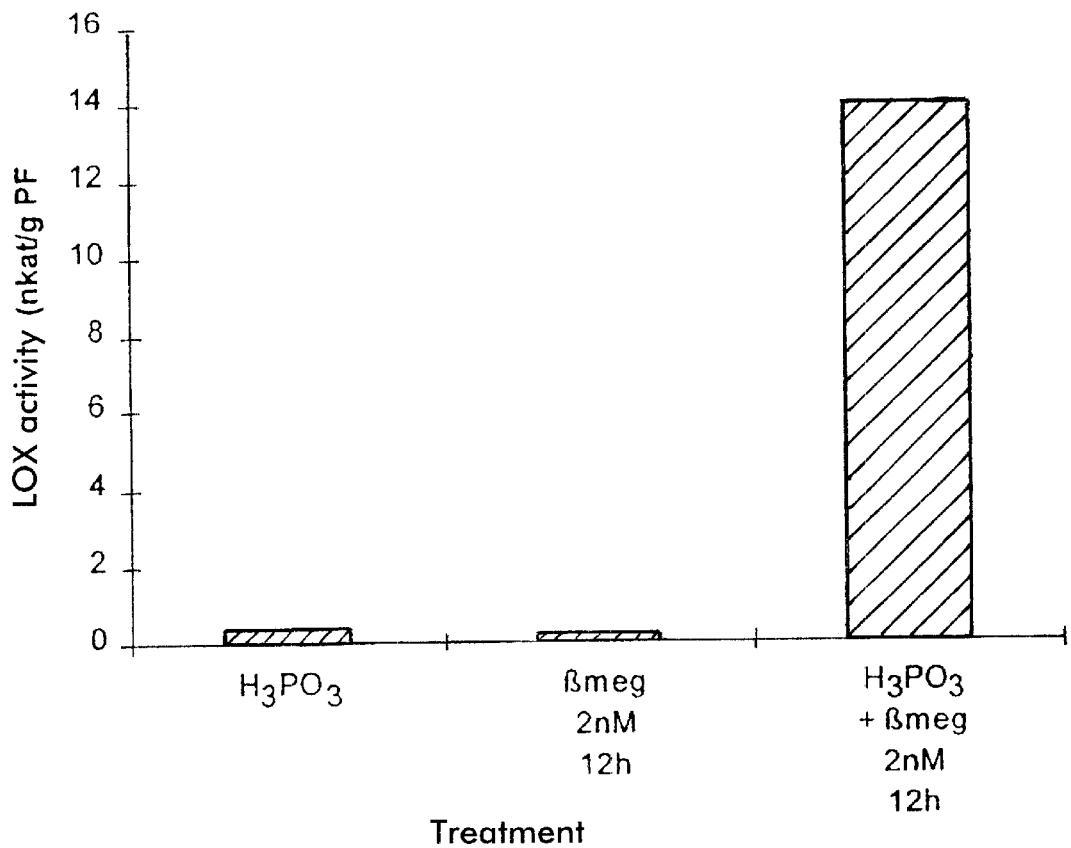
FIG. 7 shows the effect of $H_3PO_4$ on LOX.

FIG. 7. Effect of $H_3PO_3$ on the lipoxygenase (LOX) activity of tobacco cell cultures after induction with 2 nM -megaspermine.

The LOX activity was measured 12 h after elicitation with 2 nM β-megaspermine. The effect of pretreating the cells (18 h) with $H_3PO_3$, on the cell elicitability, is very large since it makes it possible to induce an LOX activity which is about 28 times greater than that of the corresponding control. No inductive effect of the LOX activity can be observed 30 h (18 h of pretreatment+12 h) after the application of $H_3PO_3$ alone.

Figure 8:
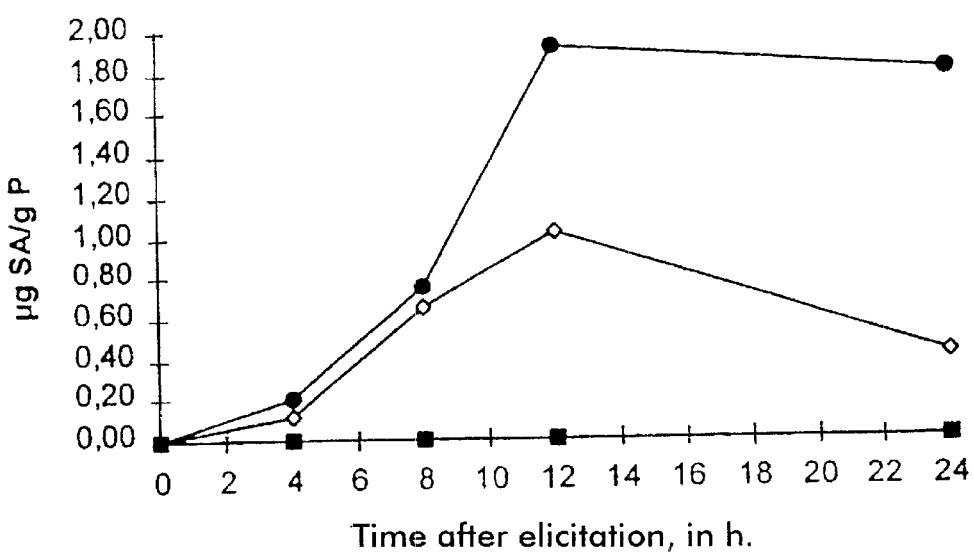
FIG. 8 shows the accumulation of SA.

FIG. 8. Accumulation of SA in tobacco cell cultures preconditioned with $H_3PO_3$ or otherwise and elicited with 5 nM β-megaspermine.

SA accumulates transiently in response to the elicitation with 5 nM β-megaspermine. Conditioning of the cells with $H_3PO_3$, 18 h before the elicitation, results in a large increase in the rate of synthesis of SA relative to that of the unconditioned cells and a persistence of the effect.

Figure 9:
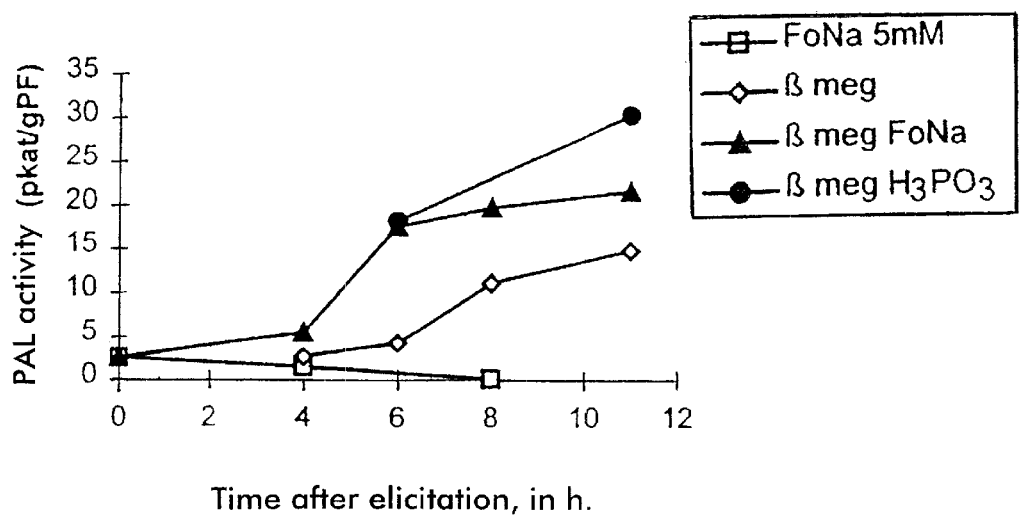
FIG. 9 shows the effect of conditioning with $H_3PO_4$ and fosetyl-Na.

FIG. 9. Effect of conditioning tobacco cell cultures with $H_3PO_3$ and fosetyl-Na on induction of the PAL activity after elicitation with 2 nM β-megaspermine.

The cell cultures were conditioned for 18 h with 5 mM $H_3PO_3$ or fosetyl-Na, and elicited with 2 nM β-megaspermine. The elicitation alone results in an increase in the PAL activity, which stabilizes 8 h after applying the elicitor. The PAL activity of the cells pretreated with $H_3PO_3$ or with fosetyl-Na is always greater than that observed in the unconditioned cells.

Conclusion: These experiments demonstrate the potentiating effect of $H_3PO_3$ and fosetyl-Na on the defense responses of tobacco. $H_3PO_3$ and fosetyl-Na do not in themselves have any effect on the PAL or LOX activity or on the synthesis of SA. The conditioning sensitizes the cell cultures to respond to low concentrations of elicitors or increases the sensitivity of the cells to the elicitors.

EXAMPLE 2

Antifungal Protection

1) Powdery Mildew/Wheat (*Erysiphe graminis* f.sp. *tritici*):

Wheat of the Victo variety (sold by the company Pionner génétique) are cultured in cold room at 10° C. with an RH of 90% and are subjected to a photoperiod of 12 h.

The plants at about three weeks old (at the stage of 2 well-developed leaves) are conditioned for one day in a greenhouse at 20° C. and watered, before treatment.

The products are applied either in sequence or as a mixture.

The dilute suspensions corresponding to a spraying volume of 250 liters of spraying liquid per hectare are prepared from the various compounds by dilution in water.

The potentiator is applied 24 h or 48 h before the elicitor, in the case of a sequential treatment.

The contamination takes place 2 days, 4 days or 5 days after treatment with the elicitor. It is effected by brushing the plants with wheat plants precontaminated the week before and which show a pulverulent conidian carpet (obligatory pathogen which does not tolerate free water to become installed).

After this contamination, the wheat plants are incubated for 7 days at 20° C. under an atmosphere of 85% RH.

2) Powdery Mildew of Grapevine (*Plasmopara viticola*)

Cuttings of grapevine (*Vitis vinifera*), Chardonnay variety, are cultured in pots in a greenhouse. When these plants are 2 months old (4–5 leaf stage), they are placed in subirrigation for one week before treatment in a greenhouse at 20° C. in order to avoid any effect of stress.

The products are applied either in sequence or as a mixture.

The dilute suspensions corresponding to a spraying volume of 500 liters of spraying liquid per hectare are prepared from the various compounds by dilution in water.

The potentiator is applied 6 days before the elicitor, in the case of a sequential treatment.

The contamination takes place 6 days after the treatment with the elicitor. It is effected by spraying an aqueous suspension of *Plasmopara viticola* spores obtained from sporulated leaves contaminated 7 days previously. These spores are suspended in a proportion of 100,000 units per $cm^3$.

The contaminated plants are then incubated for 7 days in a mist-type humid atmosphere at 18–20° C.

The reading is carried out 7 days after the contamination, by comparison with untreated but contaminated control plants. The area of the leaves showing a whitish duvet, corresponding to the sporulation of the fungus, on their underside is estimated visually.

The efficacy of the treatment product(s) is calculated from the level of sporulated leaf area and by means of the Abbott formula, this efficacy being established on three leaves per plant and three plants per test factor.

Figure 10:
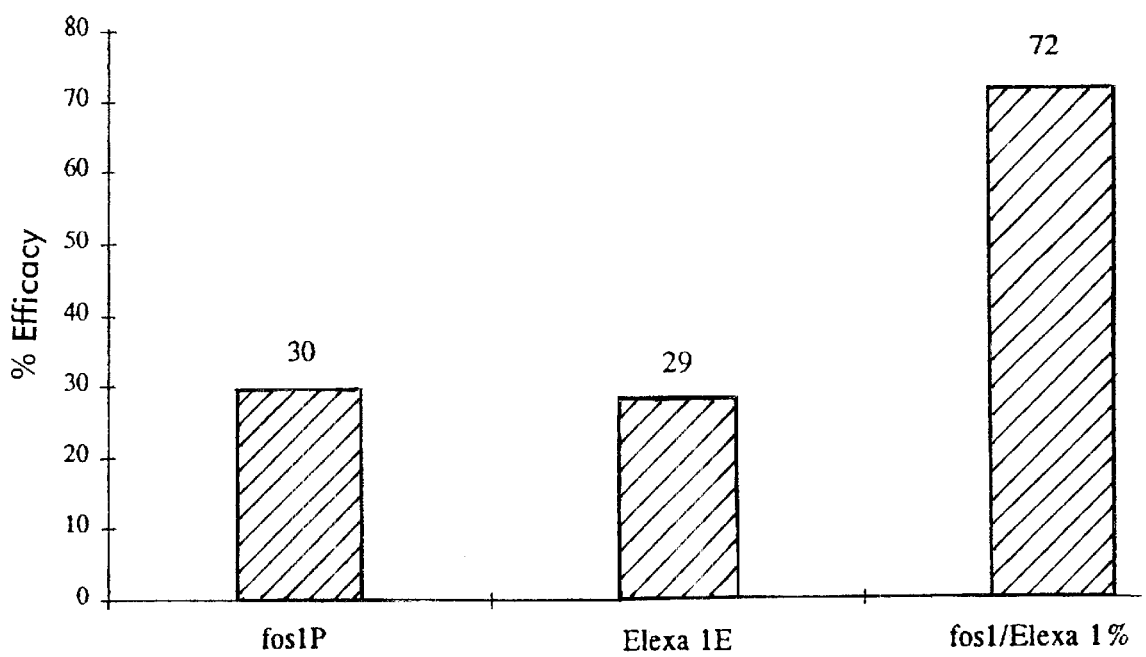
FIG. 10 shows the effect of conditioning with fosetyl-Na.

Results: Reference will be made to FIGS. 10 to 20, for which the following comments are given:

FIG. 10. Effect of the conditioning of wheat plants with fosetyl-Al applied at 1 kg/ha (Aliette WG 80%) on the development of powdery mildew after induction with an elicitor of Elexa™ carbohydrate type at 1% in the application broth supplemented with the wetting agent R56 at 0.1%.

The Colby analysis demonstrates a synergistic effect between fosetyl-Al and Elexa™ supplemented with R56 under the test conditions, against powdery mildew of wheat (*Erysiphe graminis* f. sp. *tritici*).

|  | Fosetyl-Al (1 kg/ha) × 1% Elexa ™ + 0.1% R56 |
| --- | --- |
| % Efficacy observed | 72 |
| Theoretical Colby | 50.3 |
| Synergism | + |

Figure 11:
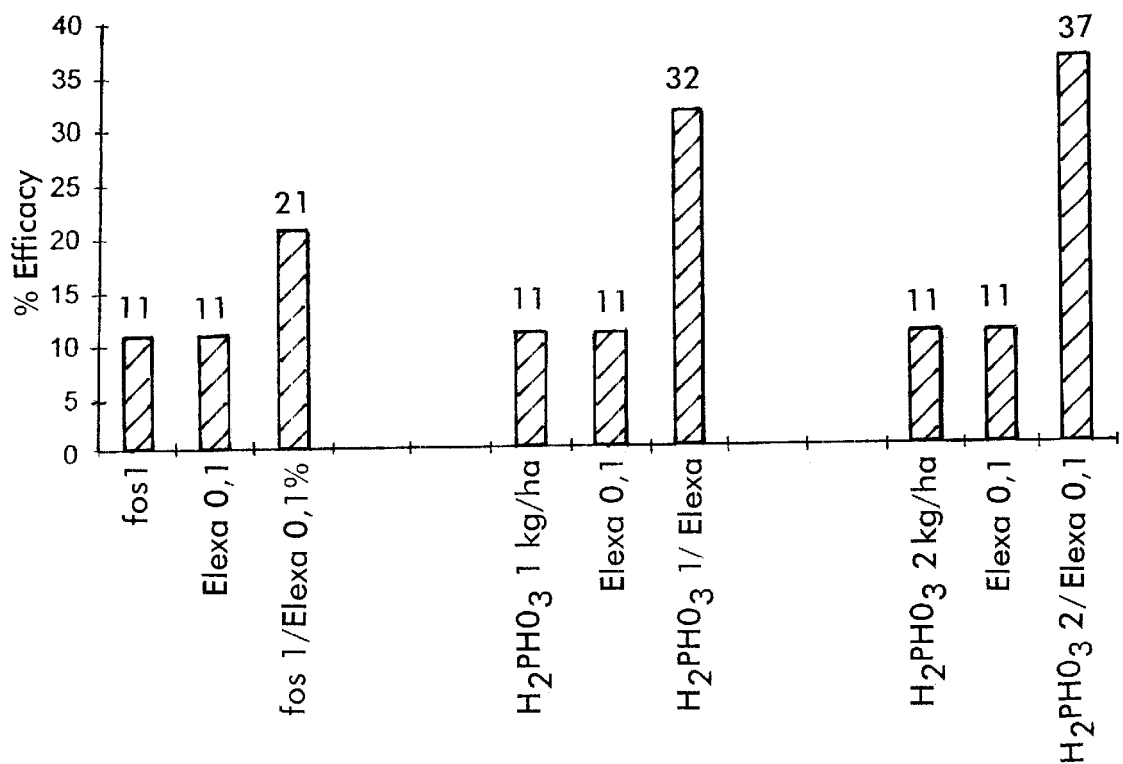
FIG. 11 shows the effect of conditioning with $H_3PO_4$ and fosetyl-Na.

FIG. 11. Synergistic effect between fosetyl-Al applied at 1 kg/ha or $H_2PHO_3$ applied at 1 or 2 kg/ha and the product Elexa™ applied as elicitor at 0.1%, supplemented with 0.1% R56 in the application broth, with respect to powdery mildew of wheat.

In this test, the reading of the symptoms was carried out on the first, second and third leaves of 24 wheat plants distributed in three pots; 48 hours separated the application of the potentiator (fosetyl-Al or $H_2PHO_3$) and the application of the elicitor Elexa™ at 0.1% supplemented with R56 at 0.1%.

|  | Fosetyl-Al (1 kg/ha) × 0.1% Elexa ™ + 0.1% R56 | $H_2PHO_3$ (1 kg/ha) × 0.1% Elexa ™ + 0.1% R56 | $H_2PHO_3$ (2 kg/ha) × 0.1% Elexa ™ + 0.1% R56 |
| --- | --- | --- | --- |
| % Efficacy observed | 21 | 32 | 37 |
| Theoretical Colby | 20.7 | 20.7 | 20.7 |
| Synergism | + | + | + |

Figure 12:
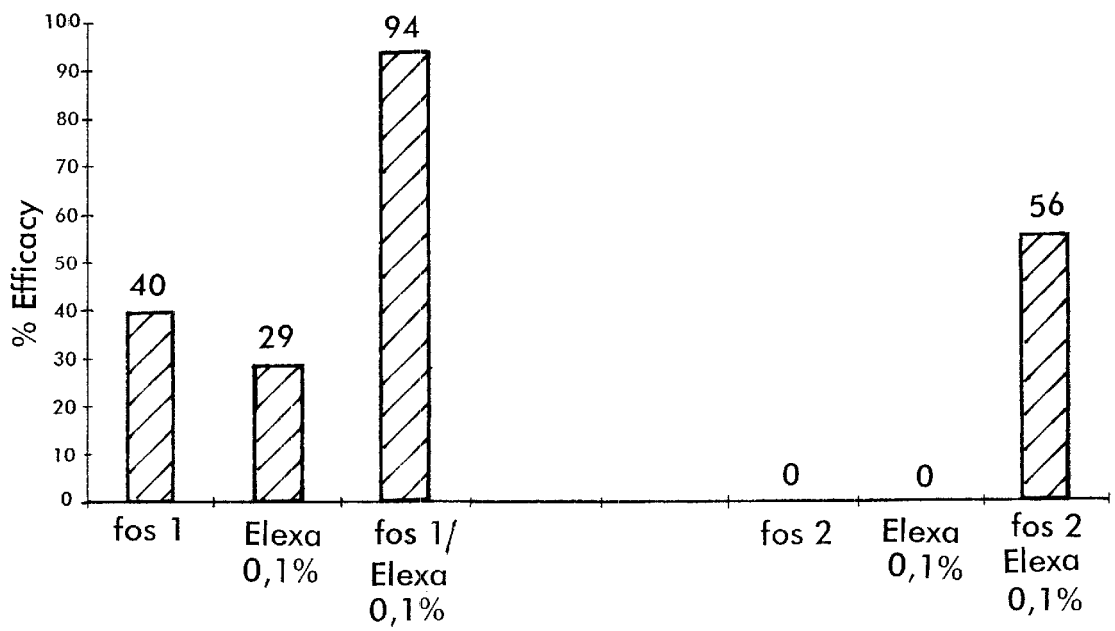
FIG. 12 shows the potentiating effect of fosetyl-Na.

FIG. 12. Potentiating effect of fosetyl-Al at 1 or 2 kg/ha after elicitation with 0.1% Elexa™ supplemented with 0.1% R56 in the application broth, against downy mildew of grapevine.

In two independent tests, a synergism of the fosetyl-Al× 0.1% Elexa™ (+0.1% R56) combination is found by Colby analysis.

|  | Fosetyl-Al (1 kg/ha) × 0.1% Elexa ™ + 0.1% R56 (1st test) | Fosetyl-Al (2 kg/ha) × 0.1% Elexa ™ + 0.1% R56 (2nd test) |
| --- | --- | --- |
| % Efficacy observed | 94 | 56 |
| Theoretical Colby | 57.4 | 0 |
| Synergism | + | + |

Figure 13:
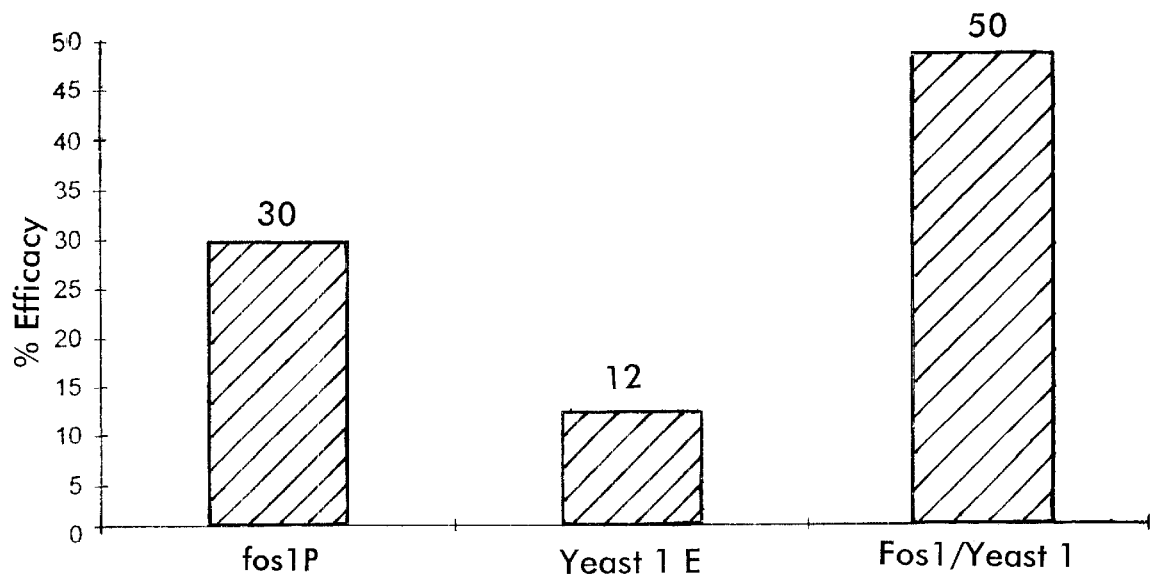
FIG. 13 shows the effect fosetyl-Na.

FIG. 13. Effect of fosetyl-Al (fos1 at 1 kg/ha) on the protection against powdery mildew of wheat after induction with an elicitor of yeast extract type at 1 g/l (yeast 1 E).

Synergism is demonstrated for the fosetyl-Al/yeast extract combination against powdery mildew of wheat, by Colby analysis.

|  | Fosetyl-Al (1 kg/ha) × yeast extract 1 g/l (Difco ™ yeast extract) |
| --- | --- |
| % Efficacy observed | 72 |
| Theoretical Colby | 38.4 |
| Synergism | + |

Figure 14:
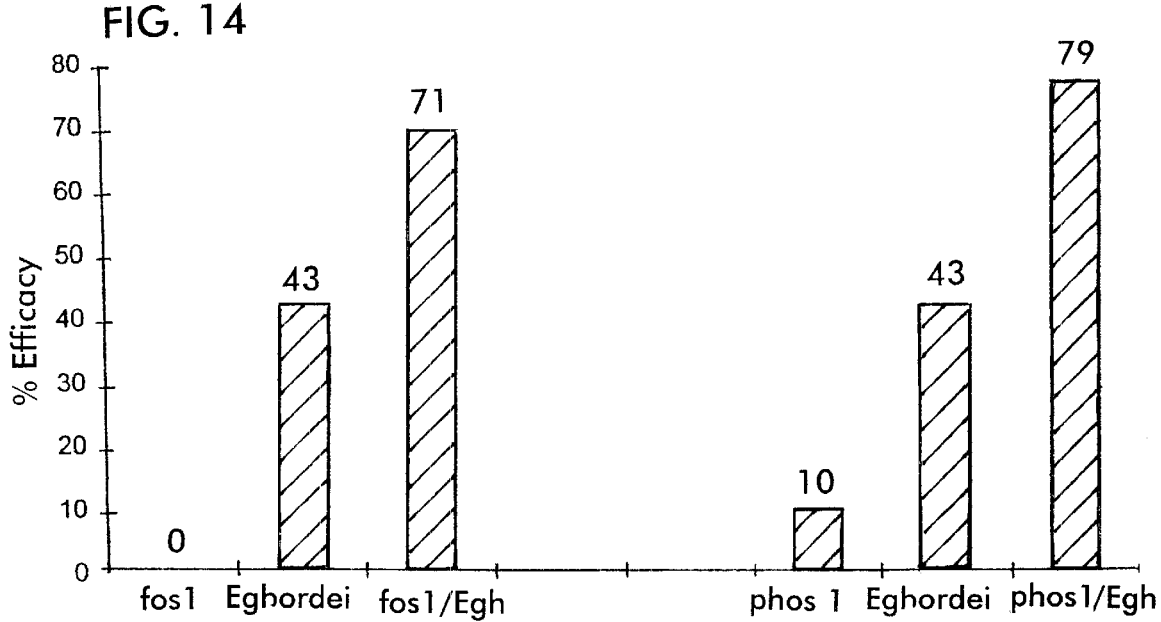
FIG. 14 shows the effect of conditioning with $H_2PO_3$ and fosetyl-Na.

FIG. 14. Effect of conditioning wheat plants with fosetyl-Al or phosphorous acid ($H_2PHO_3$) on powdery mildew of wheat after elicitation with an elicitor such as killed or live spores of a non-host fungus (*Erysiphe graminis* f. sp. *hordei*) responsible for powdery mildew of barley.

|  | Fosetyl-Al (1 kg/ha) × *Erysiphe graminis* f. sp. *hordei* | $H_2PHO_3$ (1 kg/ha) × *Erysiphe graminis* f. sp. *hordei* |
| --- | --- | --- |
| % Efficacy observed | 71 | 79 |
| Theoretical Colby | 43 | 40.5 |
| Synergism | + | + |

Synergism is demonstrated in the two cases in which the potentiator is either fosetyl-Al or $H_2PHO_3$ and the elicitor of the spores of a non-host fungus on wheat, by Colby analysis.

Figure 15:
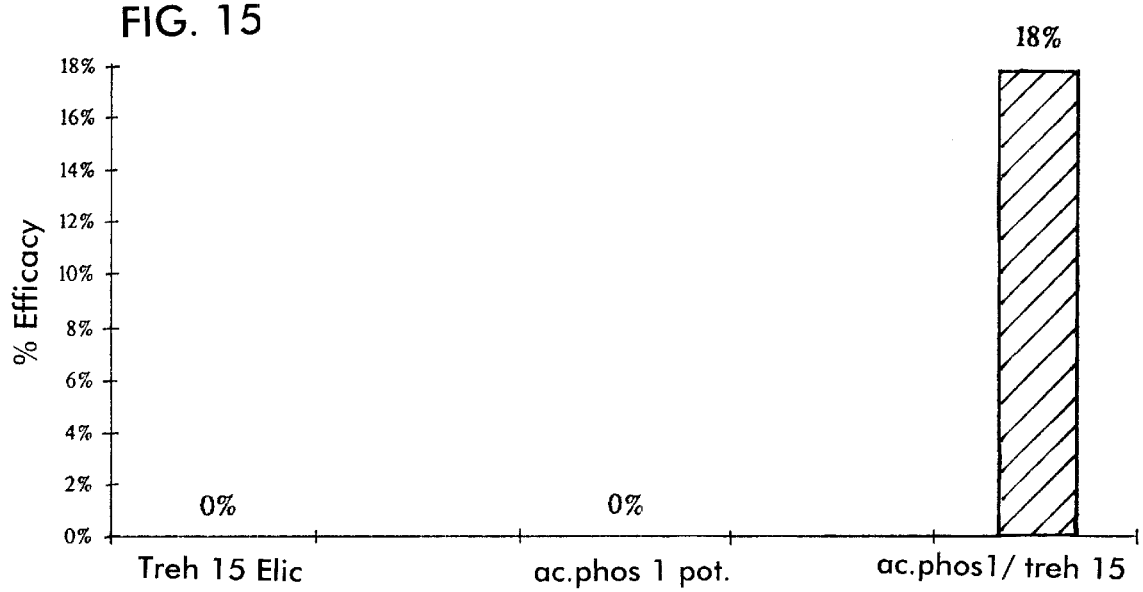
FIG. 15 shows the effect of $H_2PO_3$.

FIG. 15. Effect of $H_2PHO_3$ (1 kg/ha) on the protection of wheat plants against powdery mildew after induction with an oligosaccharide elicitor such as trehalose at 15 g/l (Prolabo).

|  | $H_2PHO_3$ (1 kg/ha) × trehalose 15 g/l (Prolabo) |
| --- | --- |
| % Efficacy observed | 18 |
| Theoretical Colby | 0 |
| Synergy | + |

A synergistic effect is observed by combining the potentiating effect of the phosphorous acid and the eliciting effect of trehalose with respect to powdery mildew of wheat, by Colby analysis.

Figure 16:
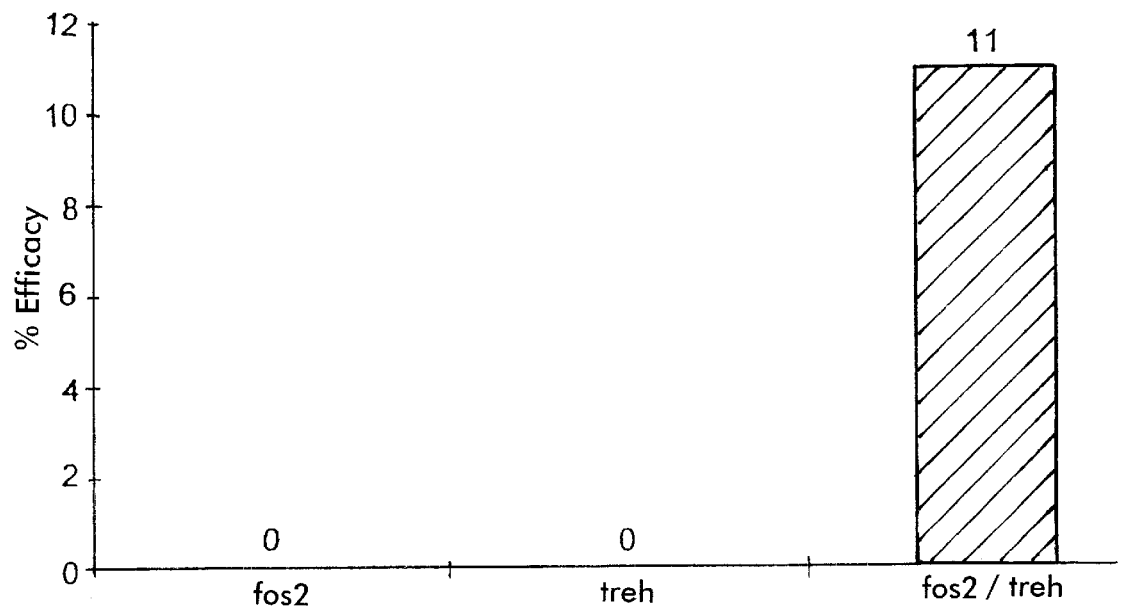
FIG. 16 shows the effect of conditioning with $H_2PO_3$.

FIG. 16. Effect of fosetyl-Al (2 kg/ha) on downy mildew of grapevine after induction with an oligosaccharide elicitor, trehalose, at 15 g/l (Prolabo).

|  | Fosetyl-Al (2 kg/ha) × trehalose 15 g/l (prolabo) |
| --- | --- |
| % Efficacy observed | 11 |
| Theoretical Colby | 0 |
| Synergy | + |

A synergistic effect is observed by combining the potentiating effect of fosetyl-Al and the eliciting effect of trehalose with respect to downy mildew of grapevine, by Colby analysis.

Figure 17:
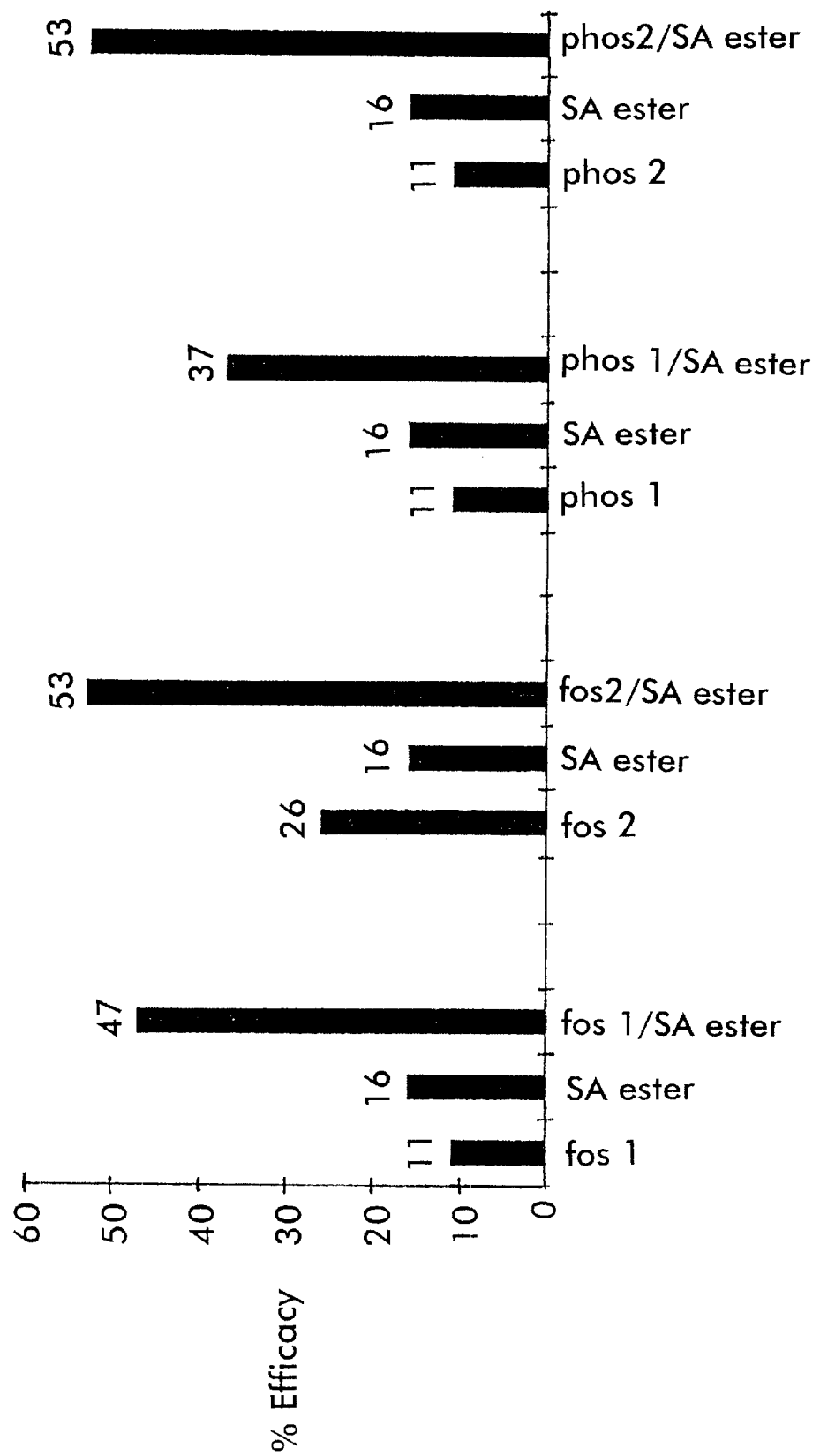
FIG. 17 shows the effect of $H_2PO_3$ or fosetyl-Na.

FIG. 17. Effect of fosetyl-Al (1 or 2 kg/ha) or $H_2PHO_3$ (1 or 2 kg/ha) on powdery mildew of wheat after induction with salicylic acid applied at 1 g/l 48 hours after the potentiator and 4 days before the contamination.

|  | Fosetyl Al (1 kg/ha) × SA ester (1 g/l) | Fosetyl Al (2 kg/ha) × SA ester (1 g/l) | $H_2PHO_3$ (1 kg/ha) × SA ester (1 g/l) | $H_2PHO_3$ (2 kg/ha) × SA ester (1 g/l) |
| --- | --- | --- | --- | --- |
| % Efficacy observed | 47 | 53 | 37 | 53 |
| Theoretical Colby | 25.2 | 37.8 | 25.2 | 25.2 |
| Synergy | + | + | + | + |

Fosetyl-Al or $H_2PHO_3$ amplify the eliciting effect of salicylic acid in a synergistic manner.

Figure 18:
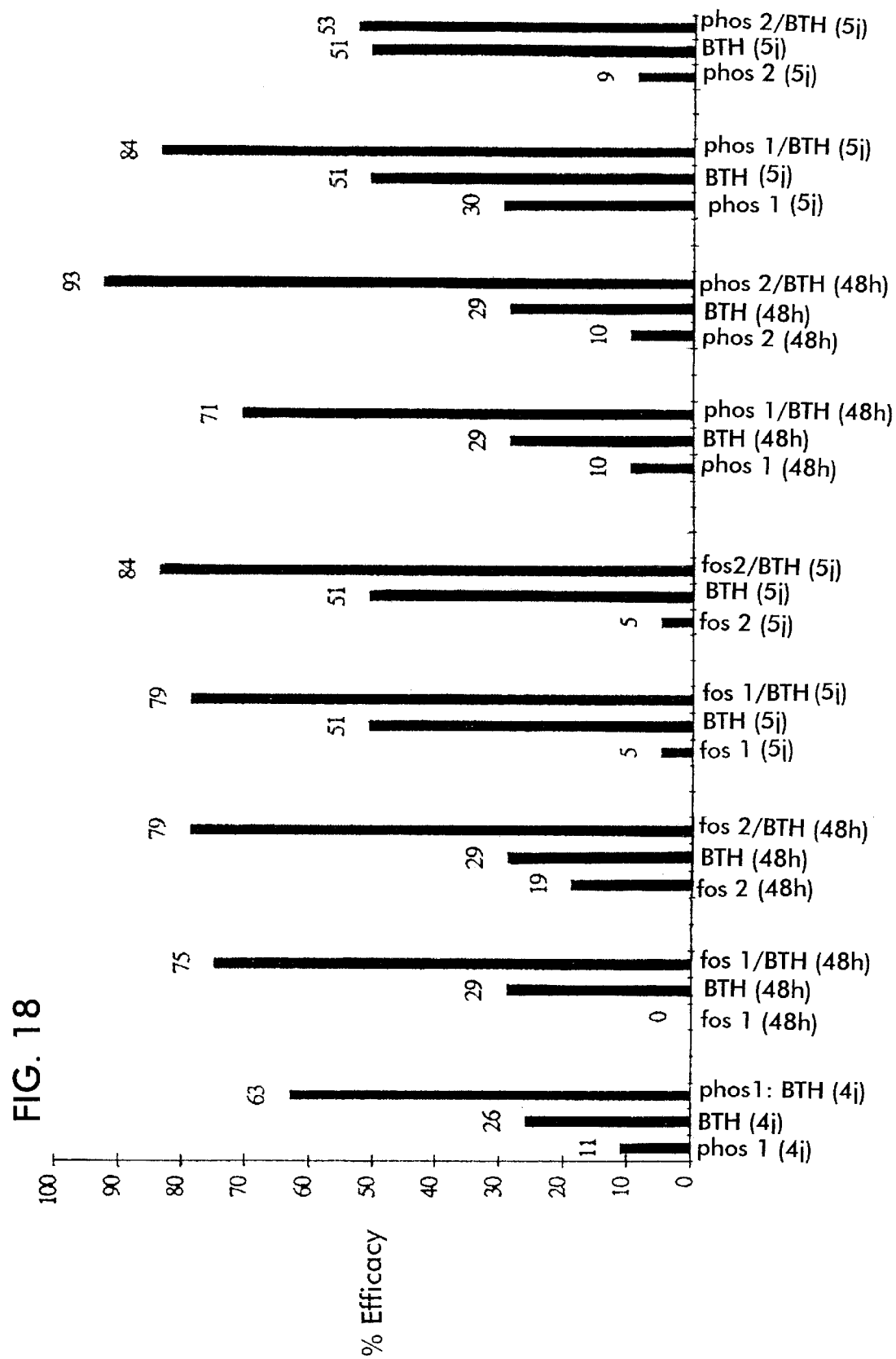
FIG. 18 shows the effect of conditioning with $H_2PO_3$.

FIG. 18. Effect of $H_2PHO_3$ (1 kg/ha) or fosetyl-Al (1 or 2 kg/ha) on powdery mildew of wheat after induction with an elicitor such as Bion™ (BTH) applied at a rate of 30 g/ha 48 hours after the potentiator and 48 hours or 4 or 5 days before the contamination.

|  | 1st test | 2nd test | | | | | | |
| --- | --- | --- | --- | --- | --- | --- | --- | --- |
|  |  | Combination | | | | | | |
| Interval between | $H_2PHO_3$ (1 kg/ha) × BTH | Fosetyl-Al (1 kg/ha) × BTH | | Fosetyl-Al (2 kg/ha) × BTH | | $H_2PHO_3$ (1 kg/ha) × BTH | | $H_2PHO_3$ (2 kg/ha) × BTH |
| elicit./cont. | 4 days | 48 h | 5 days | 48 h | 5 days | 48 h | 5 days | 48 h |
| % Efficacy observed | 63 | 75 | 79 | 79 | 84 | 71 | 84 | 93 |
| Theoretical Colby | 34 | 29 | 53.4 | 52.4 | 53.4 | 36.1 | 65.7 | 36.5 |
| Synergism | + | + | + | + | + | + | + | + |

Synergism is observed for the various combinations in which the fosetyl-Al or $H_2PHO_3$ are combined with Bion™, with respect to powdery mildew of wheat, by Colby analysis.

Figure 19:
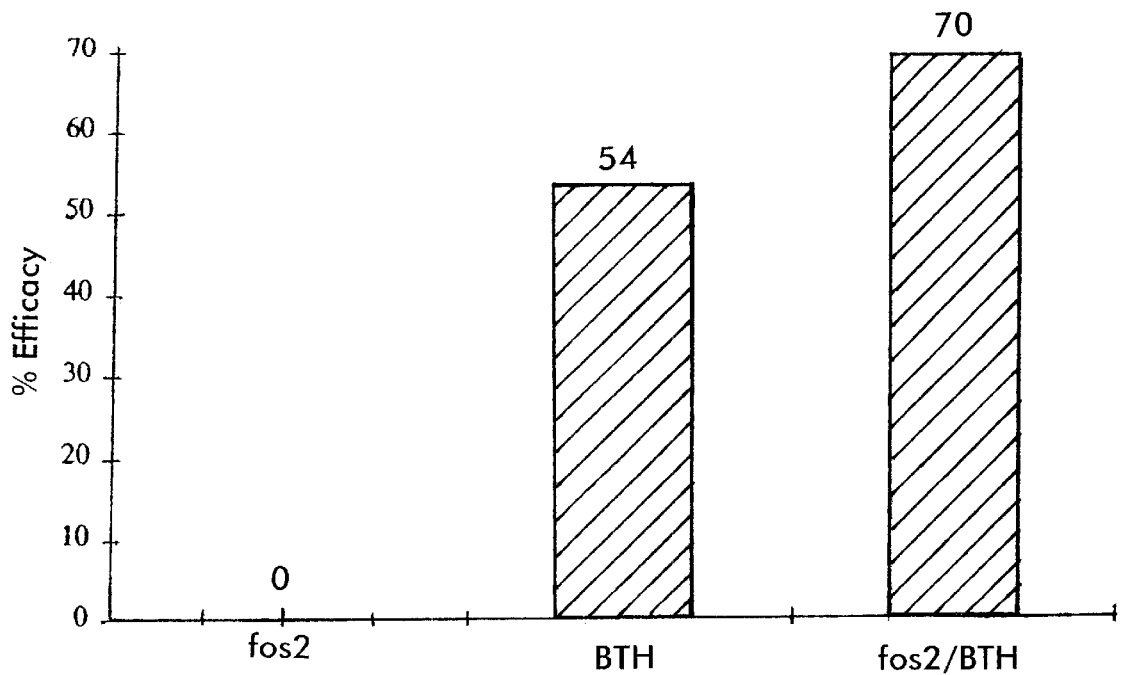
FIG. 19 shows the effect of fosetyl-Na.

FIG. 19. Effect of fosetyl-Al (2 kg/ha) combined with an elicitor such as Bion™ (BTH at 30 g/ha) on downy mildew of grapevine.

|  | Fosetyl-Al (2 kg/ha) × Bion ™ 30 g/ha |
| --- | --- |
| % Efficacy observed | 70 |
| Theoretical Colby | 54 |
| Synergy | + |

A synergist effect is observed by combining the potentiating effect of fosetyl-Al and the eliciting effect of the Bion™ with respect to downy mildew of vine, by Colby analysis.

Figure 20:
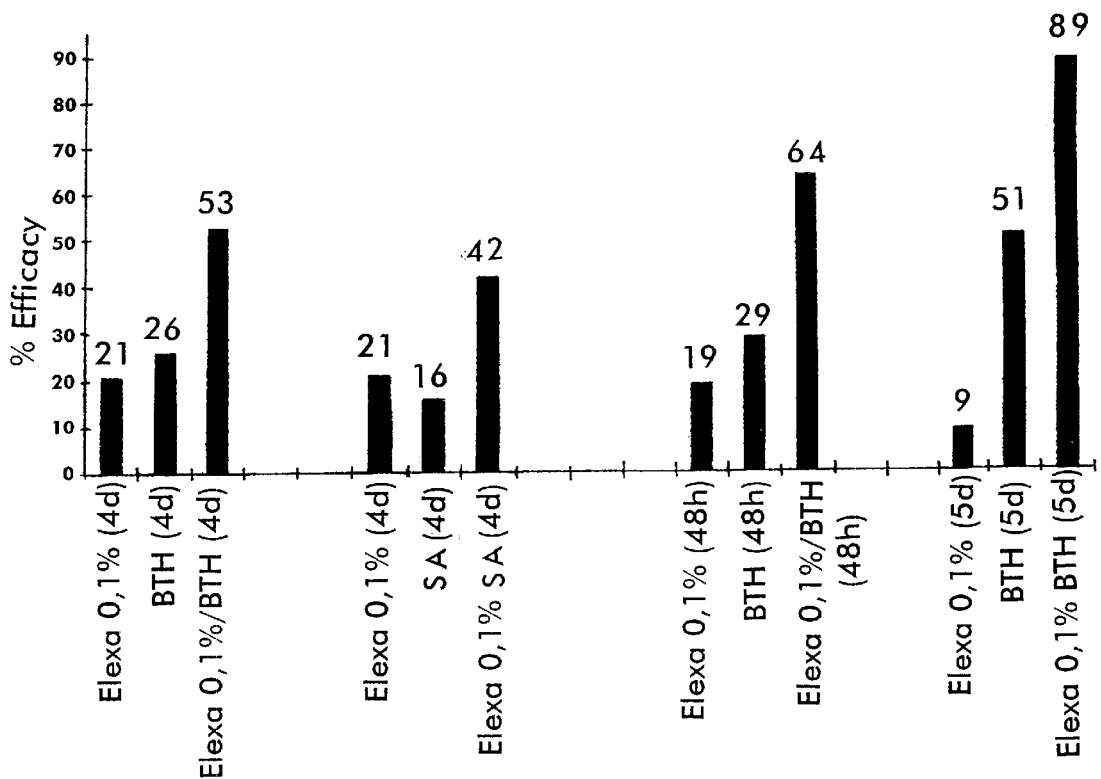
FIG. 20 shows the effect of Elexa™ (chitosan).

FIG. 20. Effect of 0.1% Elexa™ (potentiator here) supplemented with 0.1% R56 in the application broth, combined with a treatment with an elicitor such as Bion™ (BTH at 30 g/ha) or salicylic acid ester (at 1 g/l), on powdery mildew of wheat.

In the 1st test, there are 4 days between the eliciting treatment and the contamination, while in the 2nd test, the interval between applying the elicitor and contamination is either 48 hours or 5 days. In both cases, there are 48 hours between the potentiating and eliciting treatments.

|  | Combination | | | |
| --- | --- | --- | --- | --- |
| Interval between | 0.1% Elexa ™ × BTH | 0.1% Elexa ™ × SA ester | 0.1% Elexa ™ × BTH | |
| elicit./cont. | 4 d (test 1) | 4 d (test 1) | 48 h (test 2a) | 5 d (test 2b) |
| % Efficacy observed | 53 | 42 | 64 | 89 |
| Theoretical Colby | 41.5 | 24.5 | 42.5 | 54.4 |
| Synergism | + | + | + | + |

A synergistic effect is observed in each case, by Colby analysis. In all the cases, the Elexa™ amplifies the eliciting response of the BTH or of the salicylic acid.

FIG. 21. The activity of the PAL (enzyme) is shown by measuring the transformation of the L-phenylalanine (substrate transformed by PAL). By reading FIG. 21 and comparing the results obtained under the different conditions, it appears that the PAL activity is much higher when the cells are potentiated with BTH, Fosetyl-Na, or $H_3PO_3$ and elicited with a pectin oligomer.

It should be noted that kat is an abbreviation of katal, which represents the transformation of one mole of substrate per second. In other words, this reflects the activity of the enzyme (which transforms the substrate). As this unit is large, more manageable figures are generally obtained by expressing activities in microkatals ($\mu$kat), nanokatals (nkat), or picokatals (pkat), as in the figures.

The methodology followed for obtaining these results is described in Example 1 in the section headed "Phenylalanine ammonia lyase (PAL) activity".

Conclusions: Synergistic effects have been demonstrated, by Colby analysis, between fosetyl-Al and its derivatives and various categories of elicitors, which may be polysaccharides (Elexa™), simple sugars (trehalose), compounds such as salicylic acid and/or its esters, Bion™ (BTH) or non-host fungal spores (*Erysiphe graminis hordei*) in biological tests carried out on wheat and grapevine. Similarly, synergistic effects have been demonstrated between Elexa™ and elicitors such as Bion™ or salicylic acid and/or its esters.

These examples complement and correlate the physiological effects revealed on tobacco cells. A potentiation by Bion™ (BTH) has also been shown, in the case of tobacco, during elicitation with a pectin oligomer (cf. FIG. 21).

EXAMPLE 3

Open-field Trial on Powdery Mildew (*Erysiphe cichoracerum*) of Melon (Cucumis melo, Rochet Variety) by Foliar Treatment.

The fosetyl+algal extract combination contributes towards a large decrease in attack which is significant when compared with the use of the products applied alone at the same doses, as shown by the results in the table below.

The fungicide used is fosetyl-Al (WG applied at 1.25 kg/ha, i.e. 1000 g/ha of active material) and the algal extract (solution LC, 1 l/ha) is Agrimer 540 from the company Agrimer.

All of these products are used at a dose of 1000 g/ha and the percentage of plants attacked by the disease is determined 15 days after two treatments T1 and T2 (carried out with an interval of 7 days).

|  | % at T1 + 15 days | % at T2 + 15 days |
| --- | --- | --- |
| Untreated control | 91.7 | 95.0 |
| Fosetyl-Al | 80.0 | 80.0 |
| Agrimer 540 | 85.0 | 86.7 |
| Fosetyl-Al + Agrimer 540 | 48.3 | 48.3 |

EXAMPLE 4

Open-field Test on Powdery Mildew (*Erysiphe graminis*) of Wheat (Triticum aestivum, Winter Variety) by Foliar Treatment.

The fosetyl+algal extract combination contributes towards a significant decrease in attack when compared with the use of the products applied alone at the same rates, as shown by the results in the table below.

The fungicide used is fosetyl-Al (WG applied at 1.25 kg/ha, i.e. 1000 g/ha of active material) and the algal extract (solution LC, 1 l/ha) is Agrimer 540 from the company Agrimer.

All these products are used at a rate of 1000 g/ha and the percentage of plants attacked (% of leaves destroyed) by the disease is determined, on the one hand on a foliar stage treated semi-curatively (reading taken 22 days after the treatment T), and on the other hand on a foliar stage treated curatively (reading taken 27 days after the treatment T).

|  | (% of leaves destroyed at T + 22, semi-curative) | (% of leaves destroyed at T + 27, curative) |
| --- | --- | --- |
| Untreated control | 91.1 | 100 |
| Fosetyl-Al | 77.8 | 100 |
| Agrimer 540 | 77.8 | 100 |
| Fosetyl-Al + Agrimer 540 | 71.1 | 93.3 |

What is claimed is:

1. A method of amplifying the physiological preventive response of plants where at least one elicitor will be applied thereto which comprises application of at least one antifungal, antibacterial, or antiviral potentiator that is phosphorous acid or a derivative thereof prior to the application of said elicitor.

2. Method according to claim 1, characterized in that the potentiator is fosetyl-Na.

3. Method according to claim 1, characterized in that the potentiator is fosetyl-Al.

4. Method according to claim 3, characterized in that the elicitor is chitosan, CGA 245704, salicylic acid or an ester thereof, a yeast extract, trehalose or spores of a non-host fungus.

5. Method according to claim 1, characterized in that it further comprises application of a known fungicide, simultaneously with or separately from the application of the elicitor or the potentiator.

6. Method according to claim 1 for curatively or preventively controlling the phytopathogenic fungi or crops or for controlling bacteria or viruses, or a combination thereof, characterized in that an effective and non-phytotoxic amount of elicitor and potentiator is applied to the aerial parts of the plant.

7. Method according to claim 6, characterized in that it further comprises application of a known fungicide, simultaneously with or separately from the application of the elicitor or the potentiator.

8. Process according to claim 6, characterized in that the plant is selected from the group consisting of cereals, legumes, fruiting crops, arboriculture crops, grapevine, sunflower, beetroot, tobacco and ornamental crops.

9. Method according to claim 1, characterized in that the elicitor is selected from the group consisting of proteins, oligosaccharides, polysaccharides, lipids, glycolipids, glycoproteins, peptides, extracts from the walls of plant material, extracts from fungal material, extracts from the walls of plant material and from fungal material, fungi, CGA 245704, CGA 245704 analogue, yeast extracts, salicylic acid, salicylic acid ester and algal extracts.

* * * * *